United States Patent [19]

Lawson et al.

[11] Patent Number: 5,304,730
[45] Date of Patent: Apr. 19, 1994

[54] VIRUS RESISTANT PLANTS AND METHOD THEREFORE

[75] Inventors: Edgar C. Lawson, Labadie; James D. Weiss, High Ridge; Cynthia L. Hemenway, St. Louis; Nilgun E. Tumer, Chesterfield, all of Mo.

[73] Assignee: Monsanto Company, St. Louis, Mo.

[21] Appl. No.: 753,738

[22] Filed: Sep. 3, 1991

[51] Int. Cl.[5] .................. A01H 5/00; C12N 15/29; C12N 15/40; C12N 15/00
[52] U.S. Cl. .................... 800/205; 536/23.6; 536/23.72; 435/172.3; 800/DIG. 42; 935/10; 935/35; 935/67; 935/64
[58] Field of Search ............... 536/27, 23.6, 23.72; 435/172.3, 320.1, 235.1; 800/205; 935/10, 35, 64, 67

[56] References Cited

U.S. PATENT DOCUMENTS 4,970,168 11/1990 Tumer ........................ 435/317.1

OTHER PUBLICATIONS

Kawchuk, L. M. et al. 1990 *Molec. Plant. Microb. Interact.* vol. 3 pp. 301–307.
Tacke, E. et al. 1990, *J. Gen. Virol.* vol. 71 pp. 2265–2272.
Powell, P. A. et al. 1990 *Virology* vol. 175 pp. 124–130.
Sanger, M. et al. 1990 *Plant Molec. Biol* vol. 14 pp. 433–443.
Kay, R. et al. 1987 *Science,* vol. 236 pp. 1299–1302.
Edwards, J. W. et al. 1990 *Proc. Natl. Acad. Sci. USA* vol. 87 pp. 3459–3463.
Burpee Gardens catalog 1986, W. Atlee Burpee Co., Warminster, Pa. p. 143.

*Primary Examiner*—David T. Fox
*Assistant Examiner*—Mary E. Mosher
*Attorney, Agent, or Firm*—Janelle D. Strode; Dennis R. Hoerner, Jr.; Richard H. Shear

[57] ABSTRACT

A DNA sequence encoding a potato leafroll virus coat protein having at least one internal translation initiation codon in a different reading frame than the native PLRV coat protein DNA sequence altered to a non-initiator codon is provided. Two translation initiation sites at the start of a 17kd open reading frame in a different reading frame than the native PLRV coat protein DNA sequence are preferably altered A stronger stop codon is also provided in the modified PLRV DNA sequence. The modified DNA sequence having the internal translation initiation codons at the start of the 17kd open reading frame altered to non-initiator codons can be used in a gene to transform plants of the Solanaceae family to obtain transgenic plants resistant to PLRV. A synthetic modified potato leafroll virus DNA sequence is also provided which has the changes in the translation initiation sites and is further made to be more "plant-like". Multiple copies of the modified or synthetic modified PLRV coat protein DNA sequence driven by different promoters have also been transformed into potato with advantageous results. The modified potato leafroll virus DNA sequences of this invention are particularly useful in obtaining transgenic potato plants resistant to infection by potato leafroll virus 48 Claims, 14 Drawing Sheets

```
ATGAGTACGGTCGTGGTTAAAGGAAATGTCAATGGTGGTGTACAACAACCAAGAAGGCGA
------+---------+---------+---------+---------+---------+
MetSerThrValValValLysGlyAsnValAsnGlyGlyValGlnGlnProArgArgArg

AGAAGGCAATCCCTTCGCAGGCGCGCTAACAGAGTACAGCCAGTGGTTATGGTCACGGCC
------+---------+---------+---------+---------+---------+
ArgArgGlnSerLeuArgArgArgAlaAsnArgValGlnProValValMetValThrAla

CCTGGGCAACCCAGGCGCCGAAGACGCAGAAGAGGAGGCAATCGCCGCTCGAGAAGAACT
------+---------+---------+---------+---------+---------+
ProGlyGlnProArgArgArgArgArgArgGlyGlyAsnArgArgSerArgArgThr

GGAGTTCCCCGAGGACGAGGCTCAAGCGAGACATTCGTGTTTACAAAGGACAACCTCGTG
------+---------+---------+---------+---------+---------+
GlyValProArgGlyArgGlySerSerGluThrPheValPheThrLysAspAsnLeuVal

GGCAACTCCCAAGGAAGTTTCACCTTCGGGCCGAGTGTATCAGACTGTCCGGCATTCAAG
------+---------+---------+---------+---------+---------+
GlyAsnSerGlnGlySerPheThrPheGlyProSerValSerAspCysProAlaPheLys

GATGGAATACTCAAGGCCTACCATGAGTATAAGATCACAAGTATCTTACTTCAGTTCGTC
------+---------+---------+---------+---------+---------+
AspGlyIleLeuLysAlaTyrHisGluTyrLysIleThrSerIleLeuLeuGlnPheVal

AGCGAGGCCTCTTCCACCTCGCCCGGCTCCATCGCTTATGAGTTGGACCCCCATTGCAAA
------+---------+---------+---------+---------+---------+
SerGluAlaSerSerThrSerProGlySerIleAlaTyrGluLeuAspProHisCysLys

GTATCATCCCTCCAGTCCTACGTCAACAAGTTCCAAATTACAAAGGGCGGCGCTAAAACC
------+---------+---------+---------+---------+---------+
ValSerSerLeuGlnSerTyrValAsnLysPheGlnIleThrLysGlyGlyAlaLysThr

TATCAAGCGCGGATGATAAACGGGGTAGAATGGCACGATTCGTCTGAGGATCAGTGCCGG
------+---------+---------+---------+---------+---------+
TyrGlnAlaArgMetIleAsnGlyValGluTrpHisAspSerSerGluAspGlnCysArg

ATACTGTGGAAAGGAAATGGAAAATCTTCAGACCCCGCAGGATCTTTTAGAGTCACCATC
------+---------+---------+---------+---------+---------+
IleLeuTrpLysGlyAsnGlyLysSerSerAspProAlaGlySerPheArgValThrIle

AGAGTGGCTCTGCAAAACCCCAAATAG
------+---------+---------
ArgValAlaLeuGlnAsnProLysEnd
```

FIGURE 1

```
                   1                                                        50
Prosser LR 7       ATGAGTACGG TCGTGGTTAA AGGAAATGTC AATGGTGGTG TACAACAACC
Wageningen         ATGAGTACGG TCGTGGTTAA AGGAAATGTC AATGGCGGTG TACAACAACC
Canadian           ATGAGTACGG TCGTGGTTAA AGGAAATGTC AATGGTGGTG TACAACAACC
PV-0176            ATGAGTACGG TCGTGGTTAA AGGAAATGTC AATGGTGGTG TACAACAACC
PLRV-4             ATGAGTACGG TCGTGGTTAA AGGAAATGTC AATGGTGGTG TACAACAACC
Consensus          ATGAGTACGG TCGTGGTTAA AGGAAATGTC AATGG-GGTG TACAACAACC 51                                                       100
Prosser LR 7       AAGAAGGCGA AGAAGGCAAT CCCTTCGCAG GCGCGCTAAC AGAGTACAGC
Wageningen         AAGAAGGCGA AGAAGGCAAT CCCTTCGCAG GCGCGCTAAC AGAGTTCAGC
Canadian           AAGAAGGCGA AGAAGGCAAT CCCTTCGCAG GCGCGCTAAC AGAGTTCAGC
PV-0176            AAGGAGGCGA AGAAGGCAAT CCCTTCGCAG GCGCGCTAAC AGAGTTCAGC
PLRV-4             AAGAAGGCGA AGAAGGCAAT CCCTTCGCAG GCGCGCTAAC AGAGTTCAGC
Consensus          AAGAAGGCGA AGAAGGCAAT CCCTTCGCAG GCGCGCTAAC AGAGT-CAGC 101                                                      150
Prosser LR 7       CAGTGGTTAT GGTCACGGCC CCTGGGCAAC CCAGGCGCCG AAGACGCAGA
Wageningen         CAGTGGTTAT GGTCACGGCC CCTGGGCAAC CCAGGCGCCG AAGACGCAGA
Canadian           CAGTGGTTAT GGTCACGGCC CCTGGGCAAC CCAGGCGCCG AAGACGCAGA
PV-0176            CAGTGGTTAT GGTCACGGCC TCTGGGCAAC CCAGGCGCCG AAGACGTAGA
PLRV-4             CAGTGGTTAT GGTCACGGCC CCTGGGGAAC CCAGGCGCCG AAGACGCAGA
Consensus          CAGTGGTTAT GGTCACGGCC -CTGGG-AAC CCAGGCGCCG AAGACG-AGA 151                                                      200
Prosser LR 7       AGAGGAGGCA ATCGCCGCTC AAGAAGAACT GGAGTTCCCC GAGGACGAGG
Wageningen         AGAGGAGGCA ATCGCCGCTC AAGAAGAACT GGAGTTCCCC GAGGACGAGG
Canadian           AGAGGAGGCA ATCGCCGCTC AAGAAGAACT GGAGTTCCCC GAGGACGAGG
PV-0176            AGAGGAGGCA ATCGCCGCTC AAGAAGAACT GGAGTTCCCC GAGGACGAGG
PLRV-4             AGAGGAGGCA ATCGCCGCTC AAGAAGAACT GGAGTTCCCC GAGGACGAGG
Consensus          AGAGGAGGCA ATCGCCGCTC AAGAAGAACT GGAGTTCCCC GAGGACGAGG 201                                                      250
Prosser LR 7       CTCAAGCGAG ACATTCGTGT TTACAAAGGA CAACCTCGTG GGCAACTCCC
Wageningen         CTCAAGCGAG ACATTCGTGT TTACAAAGGA CAACCTCATG GGCAACTCCC
Canadian           CTCAAGCGAG ACATTCGTGT TTACAAAGGA CAACCTCGTG GGCAACTCCC
PV-0176            CTCAAGCGAG ACATTCGTGT TTACAAAGGA CAACCTCATG GGCAACTCCC
PLRV-4             CTCAAGCGAG ACATTCGTGT TTACAAAGGA CAACCTCGTG GGCAACACCC
Consensus          CTCAAGCGAG ACATTCGTGT TTACAAAGGA CAACCTC-TG GGCAAC-CCC 251                                                      300
Prosser LR 7       AAGGAAGTTT CACCTTCGGG CCGAGTGTAT CAGACTGTCC GGCATTCAAG
Wageningen         AAGGAAGTTT CACCTTCGGG CCGAGTCTAT CAGACTGTCC GGCATTCAAG
Canadian           AAGGAAGTTT CACCTTCGGG CCGAGTCTAT CAGACTGTCC GGCATTCAAG
PV-0176            AAGGAAGTTT CACCTTCGGG CCGAGTCTAT CAGACTGTCC GGCTTTCAAG
PLRV-4             AAGGAAGTTT CACCTTCGGG CCGAGTCTAT CAGACTGTCC GGCATTCAAG
Consensus          AAGGAAGTTT CACCTTCGGG CCGAGT-TAT CAGACTGTCC GGC-TTCAAG 301                                                      350
Prosser LR 7       GATGGAATAC TCAAGGCCTA CCATGAGTAT AAGATCACAA GTATCTTACT
Wageningen         GATGGAATAC TCAAGGCCTA CCATGAGTAT AAGATCACAA GCATCTTACT
Canadian           GATGGAATAC TCAAGGCCTA CCATGAGTAT AAGATCACAA GCATCTTACT
PV-0176            GATGGAATAC TCAAGGCCTA CCATGAGTAT AAGATCACAA GCATCTTACT
PLRV-4             GATGGAATAC TCAAGGCCTA CCATGACTAT AAGATCACAA GCATCTTACT
Consensus          GATGGAATAC TCAAGGCCTA CCATGAGTAT AAGATCACAA G-ATCTTACT
```

FIGURE 2    PAGE 1 OF 2

```
              351                                                    400
Prosser LR 7  TCAGTTCGTC AGCGAGGCCT CTTCCACCTC GCCCGGCTCC ATCGCTTATG
  Wageningen  TCAGTTCGTC AGCGAGGCCT CTTCCACCTC CTCCGGTTCC ATCGCTTATG
    Canadian  TCAGTTCGTC AGCGAGGCCT CTTCCACCTC CTCCGGTTCC ATCGCTTATG
     PV-0176  TCAGTTCGTC AGCGAGGCCT CTTCCACCTC CTCCGGCTCC ATCGCTTATG
      PLRV-4  TCAGTTCGTC AGCGAGGCCT CTTCCACCTC CTCCGGTTCC ATCGCTTATG
   Consensus  TCAGTTCGTC AGCGAGGCCT CTTCCACCTC --CCGG-TCC ATCGCTTATG 401                                                    450
Prosser LR 7  AGTTGGACCC CCATTGCAAA GTATCATCCC TCCAGTCCTA CGTCAACAAG
  Wageningen  AGTTGGACCC CCATTGCAAA GTATCATCCC TCCAGTCCTA CGTCAACCAG
    Canadian  AGTTGGACCC CCATTGCAAA GTATCATCCC TCCAGTCCTA CGTCAACAAG
     PV-0176  AGTTGGACCC CCATTGCAAA GTATCATCCC TCCAGTCCTA CGTCAACAAG
      PLRV-4  AGTTGGACCC CCATTGCAAA GTATCATCCC TCCAGTCCTA CGTCAACAAG
   Consensus  AGTTGGACCC CCATTGCAAA GTATCATCCC TCCAGTCCTA CGTCAAC-AG 451                                                    500
Prosser LR 7  TTCCAAATTA CAAAGGGCGG CGCTAAAACC TATCAAGCGC GGATGATAAA
  Wageningen  TTCCAAATTC CTCAGGGCGG CGCCAAAACT TATCAAGCGC GGATGATAAA
    Canadian  TTCCAAATTA CGAAGGGCGG CGCCAAAACT TATCAAGCGC GGATGATAAA
     PV-0176  TTCCAAATTA CGAAGGGCGG CGCCAAAACT TATCAAGCGC GGATGATAAA
      PLRV-4  TTCCAAATTA CGAAGGGCGG CGCCAAAACT TATCAAGCGC GGATGATAAA
   Consensus  TTCCAAATT- C--AGGGCGG CGC-AAAAC- TATCAAGCGC GGATGATAAA 501                                                    550
Prosser LR 7  CGGGGTAGAA TGGCACGATT CGTCTGAGGA TCAGTGCCGG ATACTGTGGA
  Wageningen  CGGGGTAGAA TGGCACGATT CTTCTGAGGA TCAGTGCCGG ATACTGTGGA
    Canadian  CGGGGTAGAA TGGCACGATT CTTCTGAGGA TCAGTGCCGG ATACTGTGGA
     PV-0176  CGGGGTAGAA TGGCACGATT CTTCTGAGGA TCAGTGCCGG ATACTGTGGA
      PLRV-4  TGGGGTAGAA TGGCACGATT CTTCTGAGGA TCAGTGTCGG ATACTGTGGA
   Consensus  -GGGGTAGAA TGGCACGATT C-TCTGAGGA TCAGTGCCGG ATACTGTGGA 551                                                    600
Prosser LR 7  AAGGAAATGG AAAATCTTCA GACCCCGCAG GATCTTTTAG AGTCACCATC
  Wageningen  AAGGAAATGG AAAATCTTCA GATACCGCAG GATCCTTCAG AGTCACCATC
    Canadian  AGGGAAATGG AAAATCTTCA GATCCCGCAG GATCCTTCAG AGTCACCATC
     PV-0176  AGGGAAATGG AAAATCTTCA GATACCGCAG GATCCTTCAG AGTCACCATC
      PLRV-4  AGGGAAATGG AAAATCTTCA GATACCGCAG GATCCTTCAG AGTCACCATC
   Consensus  A-GGAAATGG AAAATCTTCA GA--CCGCAG GATC-TTCAG AGTCACCATC 601             630
Prosser LR 7  AGAGTGGCTC TGCAAAACCC CAAATAG
  Wageningen  AGGGTGGCTT TGCAAAACCC CAAATAG
    Canadian  AGGGTGGCTT TGCAAAACCC CAAATAG
     PV-0176  AGGGTGGCTT TGCAAAACCC CAAATAG
      PLRV-4  AGGGTGGCTT TGCAAAACCC CAAATAG
   Consensus  AG-GTGGCT- TGCAAAACCC CAAATAG
```

FIGURE 2    PAGE 2 OF 2

```
ATGAGTACTGTCGTGGTTAAGGGAAACGTCAACGGTGGTGTACAACAACCTAGAAGGAGA
------+---------+---------+---------+---------+---------+
MetSerThrValValValLysGlyAsnValAsnGlyGlyValGlnGlnProArgArgArg

AGAAGGCAATCCCTTCGCAGAAGAGCTAACAGAGTACAGCCAGTGGTTATGGTCACTGCT
------+---------+---------+---------+---------+---------+
ArgArgGlnSerLeuArgArgArgAlaAsnArgValGlnProValValMetValThrAla

CCTGGCGAACCCAGGAGAAGAAGACGCAGAAGAGGAGGCAATAGAAGATCTAGAAGAACT
------+---------+---------+---------+---------+---------+
ProGlyGluProArgArgArgArgArgArgGlyGlyAsnArgArgSerArgArgThr

GGAGTTCCAAGAGGAAGAGGCTCAAGCGAGACATTCGTGTTTACAAAGGACAACCTCGTG
------+---------+---------+---------+---------+---------+
GlyValProArgGlyArgGlySerSerGluThrPheValPheThrLysAspAsnLeuVal

GGCAACTCCCAAGGAAGTTTCACCTTCGGACCAAGTGTATCAGACTGTCCAGCATTCAAG
------+---------+---------+---------+---------+---------+
GlyAsnSerGlnGlySerPheThrPheGlyProSerValSerAspCysProAlaPheLys

GATGGAATACTCAAGGCCTACCATGAGTACAAGATCACAAGTATCCTTCTTCAGTTCGTC
------+---------+---------+---------+---------+---------+
AspGlyIleLeuLysAlaTyrHisGluTyrLysIleThrSerIleLeuLeuGlnPheVal

AGCGAGGCCTCTTCCACCTCTCCAGGATCCATCGCTTATGAGTTGGATCCACATTGCAAA
------+---------+---------+---------+---------+---------+
SerGluAlaSerSerThrSerProGlySerIleAlaTyrGluLeuAspProHisCysLys

GTATCATCCCTCCAGTCCTACGTCAACAAGTTCCAAATCACAAAGGGAGGAGCTAAGACC
------+---------+---------+---------+---------+---------+
ValSerSerLeuGlnSerTyrValAsnLysPheGlnIleThrLysGlyGlyAlaLysThr

TATCAAGCTAGAATGATCAACGGAGTAGAATGGCACGATTCTTCTGAGGATCAGTGCAGA
------+---------+---------+---------+---------+---------+
TyrGlnAlaArgMetIleAsnGlyValGluTrpHisAspSerSerGluAspGlnCysArg

ATACTTTGGAAAGGAAATGGAAGATCTTCAGATCCAGCAGGATCTTTCAGAGTCACCATC
------+---------+---------+---------+---------+---------+
IleLeuTrpLysGlyAsnGlyArgSerSerAspProAlaGlySerPheArgValThrIle

AGAGTGGCTCTTCAAAACCCCAAGTAA
------+---------+---------
ArgValAlaLeuGlnAsnProLysEnd
```

FIGURE 3

```
ATGAGTACTGTCGTGGTTAAGGGAAACGTGAACGGTGGTGTTCAACAACCTAGAAGGAGA
---+---------+---------+---------+---------+---------+---------
MetSerThrValValValLysGlyAsnValAsnGlyGlyValGlnGlnProArgArgArg

AGAAGGCAATCCCTTCGTAGGAGAGCTAACAGAGTTCAGCCAGTGGTTATGGTCACTGCT
---+---------+---------+---------+---------+---------+---------
ArgArgGlnSerLeuArgArgArgAlaAsnArgValGlnProValValMetValThrAla

CCTGGGCAACCTAGAAGGAGAAGAAGGAGAAGAGGAGGTAATCGCAGATCAAGAAGAACT
---+---------+---------+---------+---------+---------+---------
ProGlyGlnProArgArgArgArgArgArgGlyGlyAsnArgArgSerArgArgThr

GGAGTTCCCAGAGGAAGAGGTTCAAGCGAGACATTCGTGTTTACAAAGGACAACCTCGTG
---+---------+---------+---------+---------+---------+---------
GlyValProArgGlyArgGlySerSerGluThrPheValPheThrLysAspAsnLeuVal

GGCAACTCCCAAGGAAGTTTCACCTTCGGACCAAGTGTTTCAGACTGTCCAGCATTCAAG
---+---------+---------+---------+---------+---------+---------
GlyAsnSerGlnGlySerPheThrPheGlyProSerValSerAspCysProAlaPheLys

GATGGAATACTCAAGGCTTACCATGAGTACAAGATCACAAGTATCTTGCTTCAGTTCGTC
---+---------+---------+---------+---------+---------+---------
AspGlyIleLeuLysAlaTyrHisGluTyrLysIleThrSerIleLeuLeuGlnPheVal

AGCGAGGCCTCTTCCACCTCTCCAGGCTCCATCGCTTATGAGTTAGATCCACATTGCAAA
---+---------+---------+---------+---------+---------+---------
SerGluAlaSerSerThrSerProGlySerIleAlaTyrGluLeuAspProHisCysLys

GTTTCATCCCTCCAGTCCTACGTCAACAAGTTCCAAATCACAAAGGGTGGTGCTAAGACC
---+---------+---------+---------+---------+---------+---------
ValSerSerLeuGlnSerTyrValAsnLysPheGlnIleThrLysGlyGlyAlaLysThr

TATCAAGCTCGTATGATCAACGGAGTTGAATGGCACGATTCTTCTGAGGATCAGTGCAGA
---+---------+---------+---------+---------+---------+---------
TyrGlnAlaArgMetIleAsnGlyValGluTrpHisAspSerSerGluAspGlnCysArg

ATCCTTTGGAAAGGAAATGGAAAGTCTTCAGATCCAGCTGGATCTTTCAGAGTTACCATC
---+---------+---------+---------+---------+---------+---------
IleLeuTrpLysGlyAsnGlyLysSerSerAspProAlaGlySerPheArgValThrIle

AGAGTTGCTCTTCAAAACCCAAAGTAATAG
---+---------+---------+
ArgValAlaLeuGlnAsnProLysEndEnd
```

FIGURE 4

```
                       Ssp1
                       ----
          TCATCAAAATATTTAGCAGCATTCCAGATTGGGTTCAATCAACAAGGTACGAGCCATATC
    6358  ---+---------+---------+---------+---------+---------+------  6417
          AGTAGTTTTATAAATCGTCGTAAGGTCTAACCCAAGTTAGTTGTTCCATGCTCGGTATAG

ACTTTATTCAAATTGGTATCGCCAAAACCAAGAAGGAACTCCCATCCTCAAAGGTTTGTA
    6418  ---+---------+---------+---------+---------+---------+------  6477
          TGAAATAAGTTTAACCATAGCGGTTTTGGTTCTTCCTTGAGGGTAGGAGTTTCCAAACAT

AGGAAGAATTCTCAGTCCAAAGCCTCAACAAGGTCAGGGTACAGAGTCTCCAAACCATTA
    6478  ---+---------+---------+---------+---------+---------+------  6537
          TCCTTCTTAAGAGTCAGGTTTCGGAGTTGTTCCAGTCCCATGTCTCAGAGGTTTGGTAAT

GCCAAAAGCTACAGGAGATCAATGAAGAATCTTCAATCAAAGTAAACTACTGTTCCAGCA
    6538  ---+---------+---------+---------+---------+---------+------  6597
          CGGTTTTCGATGTCCTCTAGTTACTTCTTAGAAGTTAGTTTCATTTGATGACAAGGTCGT

CATGCATCATGGTCAGTAAGTTTCAGAAAAAGACATCCACCGAAGACTTAAAGTTAGTGG
    6598  ---+---------+---------+---------+---------+---------+------  6657
          GTACGTAGTACCAGTCATTCAAAGTCTTTTTCTGTAGGTGGCTTCTGAATTTCAATCACC

GCATCTTTGAAAGTAATCTTGTCAACATCGAGCAGCTGGCTTGTGGGGACCAGACAAAAA
    6658  ---+---------+---------+---------+---------+---------+------  6717
          CGTAGAAACTTTCATTAGAACAGTTGTAGCTCGTCGACCGAACACCCCTGGTCTGTTTTT

AGGAATGGTGCAGAATTGTTAGGCGCACCTACCAAAAGCATCTTTGCCTTTATTGCAAAG
    6718  ---+---------+---------+---------+---------+---------+------  6777
          TCCTTACCACGTCTTAACAATCCGCGTGGATGGTTTTCGTAGAAACGGAAATAACGTTTC

ATAAAGCAGATTCCTCTAGTACAAGTGGGGAACAAAATAACGTGGAAAAGAGCTGTCCTG
    6778  ---+---------+---------+---------+---------+---------+------  6837
          TATTTCGTCTAAGGAGATCATGTTCACCCCTTGTTTTATTGCACCTTTTCTCGACAGGAC

ACAGCCCACTCACTAATGCGTATGACGAACGCAGTGACGACCACAAAAGAATTCCCTCTA
    6838  ---+---------+---------+---------+---------+---------+------  6897
          TGTCGGGTGAGTGATTACGCATACTGCTTGCGTCACTGCTGGTGTTTTCTTAAGGGAGAT

Ssp1
                                                              ----
          TATAAGAAGGCATTCATTCCCATTTGAAGGATCATCAGATACTTAACCAATATTTCTC
    6898  ---+---------+---------+---------+---------+---------+----  6954
          ATATTCTTCCGTAAGTAAGGGTAAACTTCCTAGTAGTCTATGAATTGGTTATAAAGAG
```

FIGURE 5

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 627 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
ATG  AGT  ACG  GTC  GTG  GTT  AAA  GGA  AAT  GTC  AAT  GGT  GGT  GTA  CAA  CAA        48
Met  Ser  Thr  Val  Val  Val  Lys  Gly  Asn  Val  Asn  Gly  Gly  Val  Gln  Gln
  1              5                        10                       15

CCA  AGA  AGG  CGA  AGA  AGG  CAA  TCC  CTT  CGC  AGG  CGC  GCT  AAC  AGA  GTA        96
Pro  Arg  Arg  Arg  Arg  Arg  Gln  Ser  Leu  Arg  Arg  Arg  Ala  Asn  Arg  Val
                 20                       25                       30

CAG  CCA  GTG  GTT  ATG  GTC  ACG  GCC  CCT  GGG  CAA  CCC  AGG  CGC  CGA  AGA       144
Gln  Pro  Val  Val  Met  Val  Thr  Ala  Pro  Gly  Gln  Pro  Arg  Arg  Arg  Arg
            35                       40                       45

CGC  AGA  AGA  GGA  GGC  AAT  CGC  CGC  TCG  AGA  AGA  ACT  GGA  GTT  CCC  CGA       192
Arg  Arg  Arg  Gly  Gly  Asn  Arg  Arg  Ser  Arg  Arg  Thr  Gly  Val  Pro  Arg
       50                       55                       60

GGA  CGA  GGC  TCA  AGC  GAG  ACA  TTC  GTG  TTT  ACA  AAG  GAC  AAC  CTC  GTG       240
Gly  Arg  Gly  Ser  Ser  Glu  Thr  Phe  Val  Phe  Thr  Lys  Asp  Asn  Leu  Val
 65                       70                       75                       80

GGC  AAC  TCC  CAA  GGA  AGT  TTC  ACC  TTC  GGG  CCG  AGT  GTA  TCA  GAC  TGT       288
Gly  Asn  Ser  Gln  Gly  Ser  Phe  Thr  Phe  Gly  Pro  Ser  Val  Ser  Asp  Cys
                 85                       90                       95

CCG  GCA  TTC  AAG  GAT  GGA  ATA  CTC  AAG  GCC  TAC  CAT  GAG  TAT  AAG  ATC       336
```

```
Pro Ala Phe Lys Asp Gly Ile Leu Lys Ala Tyr His Glu Tyr Lys Ile
        100                 105                 110

ACA AGT ATC TTA CTT CAG TTC GTC AGC GAG GCC TCT TCC ACC TCG CCC         384
Thr Ser Ile Leu Leu Gln Phe Val Ser Glu Ala Ser Ser Thr Ser Pro
        115                 120                 125

GGC TCC ATC GCT TAT GAG TTG GAC CCC CAT TGC AAA GTA TCA TCC CTC         432
Gly Ser Ile Ala Tyr Glu Leu Asp Pro His Cys Lys Val Ser Ser Leu
        130                 135                 140

CAG TCC TAC GTC AAC AAG TTC CAA ATT ACA AAG GGC GGC GCT AAA ACC         480
Gln Ser Tyr Val Asn Lys Phe Gln Ile Thr Lys Gly Gly Ala Lys Thr
145                 150                 155                 160

TAT CAA GCG CGG ATG ATA AAC GGG GTA GAA TGG CAC GAT TCG TCT GAG         528
Tyr Gln Ala Arg Met Ile Asn Gly Val Glu Trp His Asp Ser Ser Glu
                165                 170                 175

GAT CAG TGC CGG ATA CTG TGG AAA GGA AAT GGA AAA TCT TCA GAC CCC         576
Asp Gln Cys Arg Ile Leu Trp Lys Gly Asn Gly Lys Ser Ser Asp Pro
                180                 185                 190

GCA GGA TCT TTT AGA GTC ACC ATC AGA GTG GCT CTG CAA AAC CCC AAA         624
Ala Gly Ser Phe Arg Val Thr Ile Arg Val Ala Leu Gln Asn Pro Lys
            195                 200                 205

TAG                                                                     627

( 2 ) INFORMATION FOR SEQ ID NO:2:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GGTCGTGGTT AAAGGAAACG TCAACGGTGG TGTACAACAA CC                          42

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

GCAAACCCC AAATAAGAAT TCTCCGGATC AGAG                                    34

( 2 ) INFORMATION FOR SEQ ID NO:4:

( i ) SEQUENCE CHARACTERISTICS:
        ( A ) LENGTH: 627 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

ATG AGT ACG GTC GTG GTT AAA GGA AAC GTC AAC GGT GGT GTA CAA CAA         48
Met Ser Thr Val Val Val Lys Gly Asn Val Asn Gly Gly Val Gln Gln
  1                 5                  10                  15

CCA AGA AGG CGA AGA AGG CAA TCC CTT CGC AGG CGC GCT AAC AGA GTA         96
Pro Arg Arg Arg Arg Arg Gln Ser Leu Arg Arg Arg Ala Asn Arg Val
                20                  25                  30

CAG CCA GTG GTT ATG GTC ACG GCC CCT GGG CAA CCC AGG CGC CGA AGA         144
Gln Pro Val Val Met Val Thr Ala Pro Gly Gln Pro Arg Arg Arg Arg
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 35  |     |     |     |     | 40  |     |     |     |     | 45  |     |     |     |     |
| CGC | AGA | AGA | GGA | GGC | AAT | CGC | CGC | TCG | AGA | AGA | ACT | GGA | GTT | CCC | CGA | 192 |
| Arg | Arg | Arg | Gly | Gly | Asn | Arg | Arg | Ser | Arg | Arg | Thr | Gly | Val | Pro | Arg |     |
|     |     | 50  |     |     |     |     | 55  |     |     |     |     | 60  |     |     |     |     |
| GGA | CGA | GGC | TCA | AGC | GAG | ACA | TTC | GTG | TTT | ACA | AAG | GAC | AAC | CTC | GTG | 240 |
| Gly | Arg | Gly | Ser | Ser | Glu | Thr | Phe | Val | Phe | Thr | Lys | Asp | Asn | Leu | Val |     |
| 65  |     |     |     |     | 70  |     |     |     |     | 75  |     |     |     |     | 80  |     |
| GGC | AAC | TCC | CAA | GGA | AGT | TTC | ACC | TTC | GGG | CCG | AGT | GTA | TCA | GAC | TGT | 288 |
| Gly | Asn | Ser | Gln | Gly | Ser | Phe | Thr | Phe | Gly | Pro | Ser | Val | Ser | Asp | Cys |     |
|     |     |     |     | 85  |     |     |     |     | 90  |     |     |     |     | 95  |     |     |
| CCG | GCA | TTC | AAG | GAT | GGA | ATA | CTC | AAG | GCC | TAC | CAT | GAG | TAT | AAG | ATC | 336 |
| Pro | Ala | Phe | Lys | Asp | Gly | Ile | Leu | Lys | Ala | Tyr | His | Glu | Tyr | Lys | Ile |     |
|     |     |     |     | 100 |     |     |     |     | 105 |     |     |     |     | 110 |     |     |
| ACA | AGT | ATC | TTA | CTT | CAG | TTC | GTC | AGC | GAG | GCC | TCT | TCC | ACC | TCG | CCC | 384 |
| Thr | Ser | Ile | Leu | Leu | Gln | Phe | Val | Ser | Glu | Ala | Ser | Ser | Thr | Ser | Pro |     |
|     |     |     | 115 |     |     |     |     | 120 |     |     |     |     | 125 |     |     |     |
| GGC | TCC | ATC | GCT | TAT | GAG | TTG | GAC | CCC | CAT | TGC | AAA | GTA | TCA | TCC | CTC | 432 |
| Gly | Ser | Ile | Ala | Tyr | Glu | Leu | Asp | Pro | His | Cys | Lys | Val | Ser | Ser | Leu |     |
|     | 130 |     |     |     |     | 135 |     |     |     |     | 140 |     |     |     |     |     |
| CAG | TCC | TAC | GTC | AAC | AAG | TTC | CAA | ATT | ACA | AAG | GGC | GGC | GCT | AAA | ACC | 480 |
| Gln | Ser | Tyr | Val | Asn | Lys | Phe | Gln | Ile | Thr | Lys | Gly | Gly | Ala | Lys | Thr |     |
| 145 |     |     |     |     | 150 |     |     |     |     | 155 |     |     |     |     | 160 |     |
| TAT | CAA | GCG | CGG | ATG | ATA | AAC | GGG | GTA | GAA | TGG | CAC | GAT | TCG | TCT | GAG | 528 |
| Tyr | Gln | Ala | Arg | Met | Ile | Asn | Gly | Val | Glu | Trp | His | Asp | Ser | Ser | Glu |     |
|     |     |     |     | 165 |     |     |     |     | 170 |     |     |     |     | 175 |     |     |
| GAT | CAG | TGC | CGG | ATA | CTG | TGG | AAA | GGA | AAT | GGA | AAA | TCT | TCA | GAC | CCC | 576 |
| Asp | Gln | Cys | Arg | Ile | Leu | Trp | Lys | Gly | Asn | Gly | Lys | Ser | Ser | Asp | Pro |     |
|     |     |     | 180 |     |     |     |     | 185 |     |     |     |     | 190 |     |     |     |
| GCA | GGA | TCT | TTT | AGA | GTC | ACC | ATC | AGA | GTG | GCT | CTG | CAA | AAC | CCC | AAA | 624 |
| Ala | Gly | Ser | Phe | Arg | Val | Thr | Ile | Arg | Val | Ala | Leu | Gln | Asn | Pro | Lys |     |
|     |     | 195 |     |     |     |     | 200 |     |     |     |     | 205 |     |     |     |     |
| TAA |     |     |     |     |     |     |     |     |     |     |     |     |     |     |     | 627 |

( 2 ) INFORMATION FOR SEQ ID NO:5:

( i ) SEQUENCE CHARACTERISTICS:
        ( A ) LENGTH: 630 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| ATG | AGT | ACT | GTC | GTG | GTT | AAG | GGA | AAC | GTG | AAC | GGT | GGT | GTT | CAA | CAA | 48  |
| Met | Ser | Thr | Val | Val | Val | Lys | Gly | Asn | Val | Asn | Gly | Gly | Val | Gln | Gln |     |
| 1   |     |     |     | 5   |     |     |     |     | 10  |     |     |     |     | 15  |     |     |
| CCT | AGA | AGG | AGA | AGA | AGG | CAA | TCC | CTT | CGT | AGG | AGA | GCT | AAC | AGA | GTT | 96  |
| Pro | Arg | Arg | Arg | Arg | Arg | Gln | Ser | Leu | Arg | Arg | Arg | Ala | Asn | Arg | Val |     |
|     |     |     | 20  |     |     |     |     | 25  |     |     |     |     | 30  |     |     |     |
| CAG | CCA | GTG | GTT | ATG | GTC | ACT | GCT | CCT | GGG | CAA | CCT | AGA | AGG | AGA | AGA | 144 |
| Gln | Pro | Val | Val | Met | Val | Thr | Ala | Pro | Gly | Gln | Pro | Arg | Arg | Arg | Arg |     |
|     |     | 35  |     |     |     |     | 40  |     |     |     |     | 45  |     |     |     |     |
| AGG | AGA | AGA | GGA | GGT | AAT | CGC | AGA | TCA | AGA | AGA | ACT | GGA | GTT | CCC | AGA | 192 |
| Arg | Arg | Arg | Gly | Gly | Asn | Arg | Arg | Ser | Arg | Arg | Thr | Gly | Val | Pro | Arg |     |
|     |     | 50  |     |     |     |     | 55  |     |     |     |     | 60  |     |     |     |     |
| GGA | AGA | GGT | TCA | AGC | GAG | ACA | TTC | GTG | TTT | ACA | AAG | GAC | AAC | CTC | GTG | 240 |
| Gly | Arg | Gly | Ser | Ser | Glu | Thr | Phe | Val | Phe | Thr | Lys | Asp | Asn | Leu | Val |     |
| 65  |     |     |     |     | 70  |     |     |     |     | 75  |     |     |     |     | 80  |     |
| GGC | AAC | TCC | CAA | GGA | AGT | TTC | ACC | TTC | GGA | CCA | AGT | GTT | TCA | GAC | TGT | 288 |
| Gly | Asn | Ser | Gln | Gly | Ser | Phe | Thr | Phe | Gly | Pro | Ser | Val | Ser | Asp | Cys |     |
|     |     |     |     | 85  |     |     |     |     | 90  |     |     |     |     | 95  |     |     |
| CCA | GCA | TTC | AAG | GAT | GGA | ATA | CTC | AAG | GCT | TAC | CAT | GAG | TAC | AAG | ATC | 336 |

| | | | | | | | | | | | | | | |
|---|---|---|---|---|---|---|---|---|---|---|---|---|---|---|
| Pro | Ala | Phe | Lys<br>100 | Asp | Gly | Ile | Leu | Lys<br>105 | Ala | Tyr | His | Glu | Tyr<br>110 | Lys Ile |

| | | | | | | | | | | | | | | | |
|---|---|---|---|---|---|---|---|---|---|---|---|---|---|---|---|
| ACA | AGT | ATC | TTG | CTT | CAG | TTC | GTC | AGC | GAG | GCC | TCT | TCC | ACC | TCT CCA | 384 |
| Thr | Ser | Ile<br>115 | Leu | Leu | Gln | Phe | Val<br>120 | Ser | Glu | Ala | Ser | Ser<br>125 | Thr | Ser Pro | |

| | | | | | | | | | | | | | | | |
|---|---|---|---|---|---|---|---|---|---|---|---|---|---|---|---|
| GGC | TCC | ATC | GCT | TAT | GAG | TTA | GAT | CCA | CAT | TGC | AAA | GTT | TCA | TCC CTC | 432 |
| Gly | Ser<br>130 | Ile | Ala | Tyr | Glu | Leu<br>135 | Asp | Pro | His | Cys | Lys<br>140 | Val | Ser | Ser Leu | |

| | | | | | | | | | | | | | | | |
|---|---|---|---|---|---|---|---|---|---|---|---|---|---|---|---|
| CAG | TCC | TAC | GTC | AAC | AAG | TTC | CAA | ATC | ACA | AAG | GGT | GGT | GCT | AAG ACC | 480 |
| Gln<br>145 | Ser | Tyr | Val | Asn | Lys<br>150 | Phe | Gln | Ile | Thr | Lys<br>155 | Gly | Gly | Ala | Lys Thr<br>160 | |

| | | | | | | | | | | | | | | | |
|---|---|---|---|---|---|---|---|---|---|---|---|---|---|---|---|
| TAT | CAA | GCT | CGT | ATG | ATC | AAC | GGA | GTT | GAA | TGG | CAC | GAT | TCT | TCT GAG | 528 |
| Tyr | Gln | Ala | Arg | Met<br>165 | Ile | Asn | Gly | Val | Glu<br>170 | Trp | His | Asp | Ser | Ser Glu<br>175 | |

| | | | | | | | | | | | | | | | |
|---|---|---|---|---|---|---|---|---|---|---|---|---|---|---|---|
| GAT | CAG | TGC | AGA | ATC | CTT | TGG | AAA | GGA | AAT | GGA | AAG | TCT | TCA | GAT CCA | 576 |
| Asp | Gln | Cys | Arg<br>180 | Ile | Leu | Trp | Lys | Gly<br>185 | Asn | Gly | Lys | Ser | Ser<br>190 | Asp Pro | |

| | | | | | | | | | | | | | | | |
|---|---|---|---|---|---|---|---|---|---|---|---|---|---|---|---|
| GCT | GGA | TCT | TTC | AGA | GTT | ACC | ATC | AGA | GTT | GCT | CTT | CAA | AAC | CCA AAG | 624 |
| Ala | Gly | Ser<br>195 | Phe | Arg | Val | Thr | Ile<br>200 | Arg | Val | Ala | Leu | Gln<br>205 | Asn | Pro Lys | |

TAATAG          630

( 2 ) INFORMATION FOR SEQ ID NO:6:

( i ) SEQUENCE CHARACTERISTICS:
        ( A ) LENGTH: 597 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

| | | | | | |
|---|---|---|---|---|---|
| TCATCAAAAT | ATTTAGCAGC | ATTCCAGATT | GGGTTCAATC | AACAAGGTAC | GAGCCATATC | 60 |
| ACTTTATTCA | AATTGGTATC | GCCAAAACCA | AGAAGGAACT | CCCATCCTCA | AGGTTTGTA | 120 |
| AGGAAGAATT | CTCAGTCCAA | AGCCTCAACA | AGGTCAGGGT | ACAGAGTCTC | CAAACCATTA | 180 |
| GCCAAAAGCT | ACAGGAGATC | AATGAAGAAT | CTTCAATCAA | AGTAAACTAC | TGTTCCAGCA | 240 |
| CATGCATCAT | GGTCAGTAAG | TTTCAGAAAA | AGACATCCAC | CGAAGACTTA | AAGTTAGTGG | 300 |
| GCATCTTTGA | AAGTAATCTT | GTCAACATCG | AGCAGCTGGC | TTGTGGGGAC | CAGACAAAAA | 360 |
| AGGAATGGTG | CAGAATTGTT | AGGCGCACCT | ACCAAAAGCA | TCTTTGCCTT | TATTGCAAAG | 420 |
| ATAAAGCAGA | TTCCTCTAGT | ACAAGTGGGG | AACAAAATAA | CGTGGAAAAG | AGCTGTCCTG | 480 |
| ACAGCCCACT | CACTAATGCG | TATGACGAAC | GCAGTGACGA | CCACAAAAGA | ATTCCCTCTA | 540 |
| TATAAGAAGG | CATTCATTCC | CATTTGAAGG | ATCATCAGAT | ACTAACCAAT | ATTTCTC | 597 |

( 2 ) INFORMATION FOR SEQ ID NO:7:

( i ) SEQUENCE CHARACTERISTICS:
        ( A ) LENGTH: 627 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

| | | | | | |
|---|---|---|---|---|---|
| ATGAGTACGG | TCGTGGTTAA | AGGAAATGTC | AATGGCGGTG | TACAACAACC | AAGAAGGCGA | 60 |
| AGAAGGCAAT | CCCTTCGCAG | GCGCGCTAAC | AGAGTTCAGC | CAGTGGTTAT | GGTCACGGCC | 120 |
| CCTGGGCAAC | CCAGGCGCCG | AAGACGCAGA | AGAGGAGGCA | ATCGCCGCTC | AAGAAGAACT | 180 |
| GGAGTTCCCC | GAGGACGAGG | CTCAAGCGAG | ACATTCGTGT | TTACAAAGGA | CAACCTCATG | 240 |

| | | | | | |
|---|---|---|---|---|---|
| GGCAACTCCC | AAGGAAGTTT | CACCTTCGGG | CCGAGTCTAT | CAGACTGTCC | GGCATTCAAG | 300
| GATGGAATAC | TCAAGGCCTA | CCATGAGTAT | AAGATCACAA | GCATCTTACT | TCAGTTCGTC | 360
| AGCGAGGCCT | CTTCCACCTC | CTCCGGTTCC | ATCGCTTATG | AGTTGGACCC | CCATTGCAAA | 420
| GTATCATCCC | TCCAGTCCTA | CGTCAACCAG | TTCCAAATTC | CTCAGGGCGG | CGCCAAAACT | 480
| TATCAAGCGC | GGATGATAAA | CGGGGTAGAA | TGGCACGATT | CTTCTGAGGA | TCAGTGCCGG | 540
| ATACTGTGGA | CGGGGTAGAA | TGGCACGATT | CTTCTGAGGA | TCAGTGCCGG | ATACTGTGGA | 600
| AGGGTGGCTT | TGCAAAACCC | CAAATAG | | | | 627

(2) INFORMATION FOR SEQ ID NO:8:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

| | | | | | |
|---|---|---|---|---|---|
| ATGAGTACGG | TCGTGGTTAA | AGGAAATGTC | AATGGTGGTG | TACAACAACC | AAGAAGGCGA | 60
| AGAAGGCAAT | CCCTTCGCAG | GCGCGCTAAC | AGAGTTCAGC | CAGTGGTTAT | GGTCACGGCC | 120
| CCTGGGCAAC | CCAGGCGCCG | AAGACGCAGA | AGAGGAGGCA | ATCGCCGCTC | AAGAAGAACT | 180
| GGAGTTCCCC | GAGGACGAGG | CTCAAGCGAG | ACATTCGTGT | TTACAAAGGA | CAACCTCGTG | 240
| GGCAACTCCC | AAGGAAGTTT | CACCTTCGGG | CCGAGTCTAT | CAGACTGTCC | GGCATTCAAG | 300
| GATGGAATAC | TCAAGGCCTA | CCATGAGTAT | AAGATCACAA | GCATCTTACT | TCAGTTCGTC | 360
| AGCGAGGCCT | CTTCCACCTC | CTCCGGTTCC | ATCGCTTATG | AGTTGGACCC | CCATTGCAAA | 420
| GTATCATCCC | TCCAGTCCTA | CGTCAACAAG | TTCCAAATTA | CGAAGGGCGG | CGCCAAAACT | 480
| TATCAAGCGC | GGATGATAAA | CGGGGTAGAA | TGGCACGATT | CTTCTGAGGA | TCAGTGCCGG | 540
| ATACTGTGGA | AGGGAAATGG | AAAATCTTCA | GATCCCGCAG | GATCCTTCAG | AGTCACCATC | 600
| AGGGTGGCTT | TGCAAAACCC | CAAATAG | | | | 627

(2) INFORMATION FOR SEQ ID NO:9:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

| | | | | | |
|---|---|---|---|---|---|
| ATGAGTACGG | TCGTGGTTAA | AGGAAATGTC | AATGGTGGTG | TACAACAACC | AAGGAGGCGA | 60
| AGAAGGCAAT | CCCTTCGCAG | GCGCGCTAAC | AGAGTTCAGC | CAGTGGTTAT | GGTCACGGCC | 120
| TCTGGGCAAC | CCAGGCGCCG | AAGACGTAGA | AGAGGAGGCA | ATCGCCGCTC | AAGAAGAACT | 180
| GGAGTTCCCC | GAGGACGAGG | CTCAAGCGAG | ACATTCGTGT | TTACAAAGGA | CAACCTCATG | 240
| GGCAACTCCC | AAGGAAGTTT | CACCTTCGGG | CCGAGTCTAT | CAGACTGTCC | GGCTTTCAAG | 300
| GATGGAATAC | TCAAGGCCTA | CCATGAGTAT | AAGATCACAA | GCATCTTACT | TCAGTTCGTC | 360
| AGCGAGGCCT | CTTCCACCTC | CTCCGGCTCC | ATCGCTTATG | AGTTGGACCC | CCATTGCAAA | 420
| GTATCATCCC | TCCAGTCCTA | CGTCAACAAG | TTCCAAATTA | CGAAGGGCGG | CGCCAAAACT | 480
| TATCAAGCGC | GGATGATAAA | CGGGGTAGAA | TGGCACGATT | CTTCTGAGGA | TCAGTGCCGG | 540
| ATACTGTGGA | AGGGAAATGG | AAAATCTTCA | GATACCGCAG | GATCCTTCAG | AGTCACCATC | 600

```
AGGGTGGCTT TGCAAAACCC CAAATAG                                              627
```

(2) INFORMATION FOR SEQ ID NO:10:

(i) SEQUENCE CHARACTERISTICS:
        (A) LENGTH: 627 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
ATGAGTACGG TCGTGGTTAA AGGAAATGTC AATGGTGGTG TACAACAACC AAGAAGGCGA    60
AGAAGGCAAT CCCTTCGCAG GCGCGCTAAC AGAGTTCAGC CAGTGGTTAT GGTCACGGCC   120
CCTGGGGAAC CCAGGCGCCG AAGACGCAGA AGAGGAGGCA ATCGCCGCTC AAGAAGAACT   180
GGAGTTCCCC GAGGACGAGG CTCAAGCGAG ACATTCGTGT TTACAAAGGA CAACCTCGTG   240
GGCAACACCC AAGGAAGTTT CACCTTCGGG CCGAGTCTAT CAGACTGTCC GGCATTCAAG   300
GATGGAATAC TCAAGGCCTA CCATGACTAT AAGATCACAA GCATCTTACT TCAGTTCGTC   360
AGCGAGGCCT CTTCCACCTC CTCCGGTTCC ATCGCTTATG AGTTGGACCC CCATTGCAAA   420
GTATCATCCC TCCAGTCCTA CGTCAACAAG TTCCAAATTA CGAAGGGCGG CGCCAAAACT   480
TATCAAGCGC GGATGATAAA TGGGGTAGAA TGGCACGATT CTTCTGAGGA TCAGTGTCGG   540
ATACTGTGGA AGGGAAATGG AAAATCTTCA GATACCGCAG GATCCTTCAG AGTCACCATC   600
AGGGTGGCTT TGCAAAACCC CAAATAG                                      627
```

(2) INFORMATION FOR SEQ ID NO:11:

(i) SEQUENCE CHARACTERISTICS:
        (A) LENGTH: 600 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
ATGAGTACGG TCGTGGTTAA AGGAAATGTC AATGGGGTGT ACAACAACCA AGAAGGCGAA    60
GAAGGCAATC CCTTCGCAGG CGCGCTAACA GAGTCAGCCA GTGGTTATGG TCACGGCCCT   120
GGGAACCCAG GCGCCGAAGA CGAGAAGAGG AGGCAATCGC CGCTCAAGAA GAACTGGAGT   180
TCCCCGAGGA CGAGGCTCAA GCGAGACATT CGTGTTTACA AGGACAACC TCTGGGCAAC    240
CCCAAGGAAG TTTCACCTTC GGGCCGAGTT ATCAGACTGT CCGGCTTCAA GGATGGAATA   300
CTCAAGGCCT ACCATGAGTA TAAGATCACA AGATCTTACT TCAGTTCGTC AGCGAGGCCT   360
CTTCCACCTC CCGGTCCATC GCTTATGAGT TGGACCCCCA TTGCAAAGTA TCATCCCTCC   420
AGTCCTACGT CAACAGTTCC AAATTCAGGG CGGCGCAAAA CTATCAAGCG CGGATGATAA   480
AGGGGTAGAA TGGCACGATT CTCTGAGGAT CAGTGCCGGA TACTGTGGAA GGAAATGGAA   540
AATCTTCAGA CCGCAGGATC TTCAGAGTCA CCATCAGGTG GCTTGCAAAA CCCCAAATAG   600
```

VIRUS RESISTANT PLANTS AND METHOD THEREFORE

FIELD OF THE INVENTION

This invention is related, in general, to plant genetic engineering and, more particularly, to a means and method for imparting resistance to a plant from viral infection using coat protein mediated protection.

BACKGROUND OF THE INVENTION

Many agriculturally important crops are subject to infection by plant viruses. These viruses can seriously damage a crop and drastically reduce its economic value to the grower. This eventually leads to a higher cost of the goods to the ultimate consumer. Attempts to control or prevent infection of a crop by a plant virus have been made, but until recently none have been completely satisfactory. Recently, coat-protein mediated protection of a plant from infection by a virus has proved to be useful and quite satisfactory.

The potato plant is a species that is particularly subject to viral infections. Potato plants are infected by many viruses of economic importance. One of the most serious viral problems in the potato industry is infection of a potato crop with the potato leafroll virus (PLRV). Substantial economic losses are caused when the virus infects a potato crop as infection with PLRV causes a reduction in both quality and yield of the potato crop. Economic losses caused as a result of PLRV infection have been estimated to be approximately 5% of the dollar value of the total potato crop. Current management of PLRV infection of a crop involves the use of insecticides to control the aphids that transmit the virus, but this method of control is expensive and not totally effective. Potato leafroll virus is a member of the luteovirus group and is characterized as a phloem-limited spherical virus containing a positive-sense single-stranded RNA genome. The host range of PLRV is limited to members of the Solanaceae family of which potato, tobacco, tomato and peppers are the primary members. This virus is transmitted in a persistent manner by aphids. The virion capsid protein of PLRV consists of a structural gene product of approximately 23.1 kd (the coat protein) and a read-through product that is approximately 92 kd which is believed to be an aphid transmission helper component and which is believed to be a part of the virion capsid (Bahner et al. 1990).

It has been shown that expression of a plant virus capsid protein (the coat protein) in a plant can confer resistance to the homologous virus and to related viruses. (Abel et al. 1986; Cuozzo et al. 1988; Hemenway et al. 1988; Stark and Beachy 1989; Lawson et al. 1990). In these studies, the resistance to virus disease is expressed as reduced incidence of infection, delayed symptom development, reduced virus replication or titer and slower or no systemic virus movement. Expression of the virus coat protein in these transgenic plants is responsible for the observed effects in the reduction of virus disease by an as yet undetermined mechanism (Powell et al. 1990; van Dun et al. 1988).

A native (wild-type) PLRV coat protein gene has been isolated and transformed into potato plants to yield transgenic potato plants expressing the PLRV coat protein. Subsequent inoculation of the transgenic plants with PLRV resulted in infected plants which contained detectable virus antigen by ELISA, but at a low level. (Kawchuk et al. 1990) Even though the infected plants exhibited resistance to PLRV, the fact that all of the plants became infected is disadvantageous in that it allows for continued transmission of the virus and high levels of resistance could not be expected. Thus, the prior art shows no reduced incidence of infection through use of a wild-type PLRV coat protein DNA sequence in a transgenic potato plant. In other coat protein mediated protection studies, a reduced incidence of infection was an important criterion for determining whether sufficient resistance was achieved. Furthermore, no statistical significance is provided in the prior art to support the assertion that reduced PLRV antigen levels leads to reduced transmission efficiency. The values for PLRV titers in infected transgenic plants disclosed in the prior art are very closely related, yet the allegedly corresponding values for transmission efficiency from these plants are significantly varied. Thus, one can not conclude from the prior art that a significant reduction in virus transmission is obtained from transgenic plant lines expressing a native PLRV coat protein.

There is, therefore, a continuing need in the potato industry for an improved method for controlling infection by PLRV in a potato crop that provides a more effective means of preventing infection by providing transgenic plants that are highly resistant to infection by PLRV and which exhibit a reduced incidence of infection or no infection.

SUMMARY OF THE INVENTION

A novel DNA sequence encoding a potato leafroll virus coat protein has been prepared which provides improved resistance to infection by potato leafroll virus in transgenic plants expressing the DNA sequence. The PLRV coat protein DNA sequence comprises a native PLRV coat protein DNA sequence having at least one internal translation initiation codon in a different reading frame than the native PLRV coat protein DNA sequence altered to a non-initiator codon. A PLRV coat protein DNA sequence having these characteristics is referred to as a modified PLRV coat protein DNA sequence. The modified PLRV coat protein DNA sequence of the present invention may further comprise a TAA termination codon. The DNA sequence may also include a 3' TAG codon following the TAA termination codon.

In one significant aspect of the present invention, a modified DNA sequence encoding a potato leafroll virus coat protein is provided which comprises a native PLRV coat protein DNA sequence having nucleotide 27 altered from a thymidine to a cytosine, nucleotide 33 altered from a thymidine to a cytosine and nucleotide 627 altered from a guanosine to an adenosine. This DNA sequence removes internal translation initiation codons in the native PLRV DNA sequence which are in a different reading frame than the native PLRV coat protein DNA sequence and provides a stronger termination codon, TAA, than the native termination codon, TAG. This modified PLRV coat protein DNA sequence maintains the identical amino acid sequence as the native PLRV coat protein DNA sequence. A second termination codon, TAG, may also follow the TAA termination codon in the modified PLRV coat protein DNA sequence.

In another preferred embodiment of the present invention, a DNA sequence encoding a potato leafroll virus coat protein is provided which comprises a native PLRV coat protein that has been modified to alter internal translation initiation codons in a different reading frame than the native PLRV coat protein DNA sequence to non-initiator codons and to make the DNA sequence more "plant-like". A PLRV coat protein DNA sequence having these characteristics is referred to as a synthetic modified PLRV coat protein DNA sequence. In making the DNA sequence more plant-like, the native PLRV coat protein sequence has been modified according to a set of parameters for altering a non-plant DNA sequence to make it more amenable to expression in a plant cell by removing putative polyadenylation signals, limiting self-complementary sequences and using plant preferred nucleotide and codon usage. These parameters are discussed in co-pending patent application, Serial NO. 07/476,661 which was filed on Feb. 12, 1990 and is entitled "Synthetic Plant Genes and Method for Preparation", the entirety of which is incorporated herein by reference. A TAATAG tandem termination signal may also be provided at the end of this synthetic modified PLRV coat protein DNA sequence.

In a further preferred embodiment of the present invention, a plant gene comprising a full-length transcript promoter from figwort mosaic virus (FMV35S), a modified or a synthetic modified structural DNA sequence encoding a potato leafroll virus coat protein and a 3' non-translated region which encodes a polyadenylation signal is provided which can be inserted into a plant to confer high levels of resistance from infection by PLRV to the transgenic plant. Another plant gene comprising a full-length transcript promoter from cauliflower mosaic virus (CaMV35S), a modified or a synthetic modified structural DNA sequence encoding a potato leaf roll virus coat protein, and a 3' non-translated region which encodes a polyadenylation signal is also provided. This gene may also be inserted into a plant to confer resistance from infection by PLRV to the transgenic plant. Another similar plant gene is provided having the promoter from glutamine synthetase. These plant genes may be used individually in a plant to confer viral resistance or two of these genes may be inserted into a plant and used together to confer a high level of viral resistance to the transgenic plant.

In still further preferred embodiments, a method of modifying a native potato leafroll virus coat protein DNA sequence to provide improved resistance to infection by PLRV in plants expressing a modified PLRV coat protein DNA sequence is provided. The method comprises the steps of altering at least one internal translation initiation codon in the native PLRV coat protein DNA sequence which is in a different reading frame than the native PLRV coat protein DNA sequence to non-initiator codons and providing a TAA termination codon to the sequence.

A method for providing resistance to infection by PLRV to a potato plant by transforming potato plant cells with a modified or synthetic modified PLRV coat protein DNA sequence and selecting transformed potato plants which express the modified or synthetic modified PLRV coat protein DNA sequence in the plant at a level sufficient to render the plants resistant to PLRV is also provided.

It is, therefore, a primary object of the present invention to provide a modified PLRV coat protein DNA sequence that, when expressed in a potato plant, provides a reduced incidence of infection or no infection by PLRV to the plant.

It is another object of the present invention to provide a modified PLRV coat protein DNA sequence that is translated efficiently when inserted into a potato plant to produce a transgenic plant that exhibits a reduced incidence of infection by PLRV.

It is a further object of the present invention to provide a modified PLRV coat protein DNA sequence that has reduced competition between the native PLRV coat protein initiation codon and initiation codons internal to the native PLRV coat protein DNA sequence by removal of the competitive internal initiation codons.

It is a still further object of the present invention to provide a PLRV coat protein DNA sequence that has internal translation initiation codons which are in a different reading frame than the native PLRV coat protein DNA sequence altered to non-initiator codons to provide a modified PLRV coat protein DNA sequence that is capable of providing a reduced incidence of infection to PLRV in plants expressing the modified DNA sequence.

Other and further objects and advantages of the invention will be made clear or become apparent from the following description and claims when read in light of the accompanying drawings.

BRIEF DESCRIPTION OF THE DRAWINGS

FIG. 1 (SEQ ID NO. 1) illustrates the cDNA sequence and its corresponding amino acid sequence of a genomic clone from potato leafroll virus which includes the coat protein coding sequence.

FIG. 2 illustrates a comparison of five (5) different isolates of a potato leafroll virus coat protein DNA sequence and a consensus sequence.

FIG. 3 (SEQ ID NO. 4) illustrates a modified potato leafroll virus coat protein DNA sequence.

FIG. 4 (SEQ ID NO. 5) illustrates a synthetic modified potato leafroll virus coat protein DNA sequence.

FIG. 5 (SEQ ID NO. 6) illustrates the nucleotide sequence of the full-length transcript promoter from the figwort mosaic virus (FMV35S).

DESCRIPTION OF THE PREFERRED EMBODIMENTS

Figure 6:
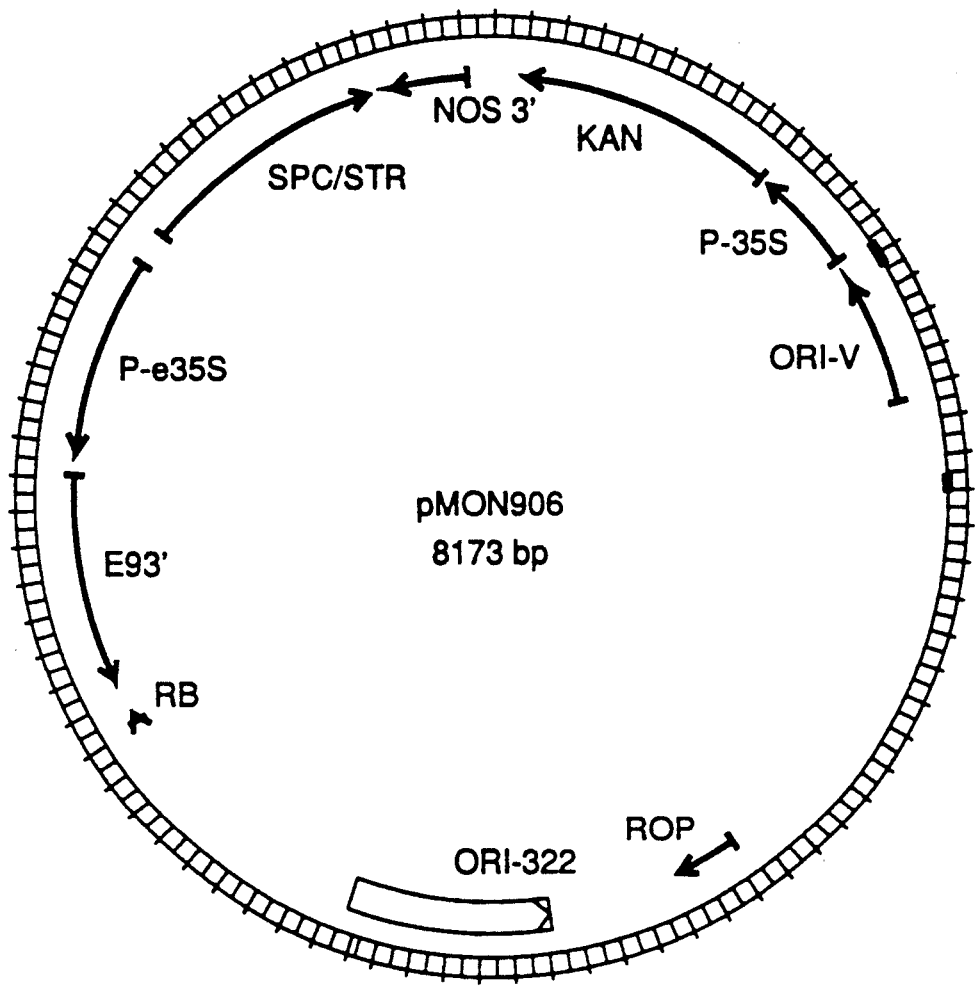
FIG. 6 illustrates a physical map of the plasmid pMON906.

A native potato leafroll virus (PLRV) coat protein DNA sequence was isolated from a cDNA library made from RNA recovered from purified PLRV virions. The PLRV isolate from which this cDNA library was made was Prosser LR7 which is a severe PLRV isolate obtained from P.E. Thomas of the United States Department of Agriculture in Prosser, WA. The cDNA nucleotide sequence of the cloned genomic fragment containing the coat protein coding sequence is shown in FIG.

1. (SEQ ID NO. 1) The PLRV coat protein coding region in FIG. 1 (SEQ ID NO. 1) is referred to as the native or wild-type PLRV coat protein DNA sequence as this is the sequence that corresponds to what occurs naturally in PLRV isolate Prosser LR7.

The cDNA coding sequence for the native PLRV coat protein comprises 624 nucleotide bases of open reading frame that encodes a protein of 208 amino acids. This coding region is referred to as SEQ ID NO 1. The amino acid sequence of the PLRV coat protein was partially determined from purified tryptic fragments by Edman degradation (Hunkapiller et al. 1983) and those sequenced fragments are underlined in FIG. 1, (SEQ ID NO. 1) whereas the remaining amino acids were deduced from the cDNA sequence. FIG. 1 (SEQ ID NO. 1) also includes the nucleotide sequence and possible amino acid sequence of the region of the PLRV genome 3' of the coat protein coding sequence.

This native PLRV coat protein DNA sequence was used as the source to produce the novel PLRV coat protein DNA sequences of this invention. The native PLRV coat protein DNA sequence was also inserted into a plant transformation vector and used in experiments which tested its ability to confer resistance to infection by PLRV in potato plants as further described in the Examples to follow.

Isolate Prosser LR7 is not the only PLRV isolate from which a native PLRV coat protein DNA sequence can be obtained. A native PLRV coat protein DNA sequence can be isolated from other PLRV isolates. The coat protein gene of PLRV shows considerable identity of sequence among various isolates and is quite homologous. FIG. 2 illustrates the considerable similarity of the DNA sequence of the PLRV coat protein among five (5) PLRV isolates including Prosser LR 7. The isolates presented in FIG. 2 were isolated from diverse geographic regions which further supports the proposition that the PLRV coat protein is highly conserved across the species even when isolated from wholly unrelated regions. In addition to Prosser LR7 which was isolated from Prosser, WA, USA, the Wagenigen PLRV is a Dutch isolate (van der Wilk et al. 1989), the Canadian isolate is from British Columbia (Kawchuk et al. 1989), the PV-0716 isolate is from Germany (Prill et al. 1988) and isolate PLRV-4 is also from British Columbia (Smith et al. 1990). As can be seen in the line designated consensus sequence in FIG. 2, the native PLRV coat protein DNA sequence is quite conserved.

The native PLRV coat protein DNA sequence of FIG. 1 (SEQ ID NO. 1) was used to obtain the novel PLRV coat protein DNA sequence with improved virus resistance characteristics of the present invention. Referring to FIG. 1, the native PLRV coat protein DNA sequence has a number of internal translation initiation codons in the DNA sequence which are in a different reading frame than the native PLRV coat protein DNA sequence. Two of these internal translation initiation codons represent the start of a 17kd open reading frame internal to the coat protein DNA sequence and in a different reading frame. These two internal translation initiation codons begin at nucleotide 26 and nucleotide 32 of the native PLRV coat protein DNA sequence and are represented by the universal translation initiation or start codon ATG. As can be seen by reference to FIG. 2, these internal translation initiation codons are highly conserved across different isolates of PLRV coat proteins. Each of the isolates in FIG. 2 show identical ATG translation initiation sites in the same location of the gene. Furthermore, the native PLRV coat protein DNA sequences each utilize a TAG termination codon as the stop codon. The presence of a TAG termination codon is also highly conserved among different PLRV isolates as it is present in each of the isolates of FIG. 2.

A preferred embodiment of the invention involves modifying a native PLRV coat protein DNA sequence such that internal translation initiation codons at the start of the 17kd open reading frame are altered to non-initiator codons and the native stop codon is altered to a stronger stop codon to prevent read through. These modifications were accomplished using site directed mutagenesis to modify the internal translation initiating sites which begin at nucleotides 26 and 32 of the native PLRV coat protein DNA sequence (SEQ ID NO 1).

In all of the isolates described in FIG. 2, the internal translation initiation codons designating the start of the 17kd open reading frame begin at nucleotides 26 and 32 and the codon is an ATG. Any PLRV isolate exhibiting the internal translation initiation codons described could be used as the starting material for preparing the novel PLRV coat protein DNA sequences of this invention. The isolate Prosser LR7 was chosen for further use in demonstrating the present invention. These ATG translation initiation codons were altered to ACG codons by site directed mutagenesis. The mutagenesis did not alter the amino acid sequence of the native PLRV coat protein, only the DNA sequence. The native PLRV coat protein DNA sequence was further modified to create a TAA termination codon in place of the termination codon TAG which is the codon beginning at nucleotide position 625 of the native PLRV coat protein coding sequence. Site directed mutagenesis was also utilized to make this change.

The nucleotide sequence of the PLRV LR-7 coat protein gene was modified using the site directed mutagenesis protocol described in Kunkel et al. (1987). A single strand template of the PLRV Prosser LR-7 cDNA containing the coat protein DNA sequence was produced from pIBI76 using R408 helper phage and grown in BW313 E. coli cells. The template was annealed with two synthetic DNA single strand oligonucleotides complementary to the ssDNA PLRV coat protein nucleotide sequence. The synthetic DNA oligonucleotides are referred to as mutagenesis primers. A copy of the coat protein DNA sequence including the nucleotide modifications contained in the mutagenesis primers is made by adding Klenow polymerase (pol I large fragment) and T4 DNA ligase with excess nucleotide triphosphate mix. The mutagenesis primer used to modify the internal translation initiation codons was:

5'
GGTCGTGGTTAAAGGAAACGT-
CAACGGTGGTGTACAACAACC. (SEQ ID
NO 2)

The mutagenesis primer used to modify the termination codon was:

5'
GCAAAACCCCAAATAAGAATTCTCC-
GGATCAGAG. (SEQ ID NO 3)

A PLRV coat protein modified in this manner is referred to hereinafter as a modified PLRV coat protein DNA sequence. This modified PLRV coat protein DNA sequence can be inserted into an appropriate plant transformation vector and used to confer resistance to infection by PLRV in plants expressing this modified PLRv coat protein DNA sequence. The DNA sequence of the modified PLRV coat protein DNA sequence is presented in FIG. 3 and is represented as SEQ ID NO 4.

A synthetic modified (SEQ ID NO. 5) PLRV coat protein DNA sequence was also prepared as a second embodiment of this invention. This synthetic modified (SEQ ID NO. 5) PLRV coat protein gene was designed to incorporate nucleotide changes to facilitate the expression of the gene in plants, to remove the internal translation initiation codons at the start of the 17kd open reading frame in a different reading frame than the PLRV coat protein DNA sequence, and to change the native stop codon to a stronger stop codon. The purpose of the modifications to the DNA sequence is to make the non-plant gene more "plant-like" by removing putative polyadenylation signals, limiting self-complementary sequences and by modifying particular nucleotides in the DNA sequence of the gene to nucleotides that are typical or preferred in a native plant gene. Once the "non-plant-like" nucleotides are identified, they may be modified by site-directed mutagenesis of the native PLRV coat protein DNA sequence using the appropriate oligonucleotides or a synthetic PLRV coat protein DNA sequence may be prepared *de novo* by oligonucleotide synthesis by methods known to those skilled in the art. This synthetic gene also contains the nucleotide changes made in the modified PLRV coat protein (SEQ ID NO. 4) DNA sequence that alter the internal translation initiation codons to non-initiator codons and places a TAA termination codon in place of the termination codon TAG in the native PLRV coat protein DNA sequence. In addition, a TAG codon is placed behind the TAA termination codon to create a tandem translational stop signal. This synthesized PLRV coat protein DNA sequence is referred to as the synthetic modified PLRV coat protein DNA sequence and is illustrated in FIG. 4 and identified as SEQ ID NO 5.

In general, to make an existing structural coding sequence ("structural gene") which codes for a particular protein more plant-like, ATTTA sequences and putative polyadenylation signals are removed by site directed mutagenesis of the DNA comprising the structural gene. It is most preferred that substantially all the polyadenylation signals and ATTTA sequences be removed although enhanced expression levels are observed with only partial removal of either of the above identified sequences. Alternately, if the synthetic gene is prepared which codes for the expression of the subject protein, codons are selected to avoid the ATTTA sequence and putative polyadenylation signals. Putative polyadenylation signals include, but are not necessarily limited to, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA. In replacing the ATTTA sequences and polyadenylation signals, codons are preferably utilized which avoid the codons which are rarely found in plant genomes.

A method for the modification of an existing structural gene or alternately the de novo synthesis of a structural gene which is somewhat less rigorous than the method described above involves scanning the selected DNA sequence to identify regions with greater than four consecutive adenine (A) or thymine (T) nucleotides. The A+T regions are scanned for potential plant polyadenylation signals. Although the absence of five or more consecutive A or T nucleotides eliminates most plant polyadenylation signals, if there are more than one of the minor polyadenylation signals identified within ten nucleotides of each other, then the nucleotide sequence of this region is preferably altered to remove these signals while maintaining the original encoded amino acid sequence.

The second step is to consider the 15 to 30 nucleotide regions surrounding the A+T rich region identified in step one. If the A+T content of the surrounding region is less than 80%, the region should be examined for polyadenylation signals. Alteration of the region based on polyadenylation signals is dependent upon (1) the number of polyadenylation signals present and (2) presence of a major plant polyadenylation signal.

The extended region is examined for the presence of plant polyadenylation signals. The polyadenylation signals are removed by site-directed mutagenesis of the DNA sequence. The extended region is also examined for multiple copies of the ATTTA sequence which are also removed by mutagenesis.

It is also preferred that regions comprising many consecutive A+T bases or G+C bases be disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

The modified or synthetic modified PLRV coat protein DNA sequences may be inserted into a suitable plant transformation vector for transformation into the desired plant species. Suitable plant transformation vectors include those derived from a Ti plasmid of *Agrobacterium tumefaciens*, as well as those disclosed, e.g., by Herrera-Estrella (1983), Bevan (1984), Klee (1985) and U.S. Pat. NO. 4,940,838, issued to Schilperoort et al. A plant transformation vector preferably includes all of the necessary elements needed for transformation of plants or plant cells. Typical plant cloning vectors comprise selectable and scoreable marker genes, T-DNA borders, cloning sites, appropriate bacterial genes to facilitate identification of transconjugates, broad host-range replication and mobilization functions and other elements as desired.

The modified or synthetic modified PLRV coat protein structural DNA sequence is inserted into a plant transformation vector as a gene capable of being expressed in a plant. For the purposes of this invention, a "gene" is defined as an element or combination of elements that is capable of being expressed in a plant, either alone or in combination with other elements. Such a gene generally comprises, in sequence, a promoter which functions in plant cells, a 5' non-translated leader sequence, a structural DNA sequence coding for the desired protein, and a 3' non-translated region which functions in plants to cause the addition of polyadenylated nucleotides to the 3' end of the RNA sequence, each element being operably coupled to the adjacent element. A plant gene comprising the above elements may be inserted by standard recombinant DNA methods known to those skilled in the art into a plant transformation vector. Alternately, some or all of the elements of the plant gene may be present in the plant transformation vector and the remaining elements added to the vector when necessary. A plant transformation vector may be prepared that has all of the necessary elements for plant expression except the desired structural DNA sequence which can readily be added to the vector by known methods.

Promoters which are known or found to cause transcription of DNA in plant cells can be used in the present invention. Such promoters may be obtained from a variety of sources such as plants or plant DNA viruses and include, but are not necessarily limited to, promoters isolated from the caulimovirus group such as the cauliflower mosaic virus 35S (CaMV35S) and the figwort mosaic virus full-length transcript promoter (FMV35S) (SEQ ID NO. 6). Other useful promoters include promoters which are highly expressed in phloem and vascular tissue of plants such as the glutamine synthase promoter (Edwards et al. 1990), the maize sucrose synthase 1 promoter (Yang et al. 1990), the promoter from the Rol-C gene of the TL DNA of Ri plasmid (Sugaya et al. 1989) and the phloem specific region of the pea RBC-S-3A promoter (Aoyagi et al. 1988).

The particular promoter selected should be capable of causing sufficient expression to result in the production of an effective amount of the PLRV coat protein polypeptide to render the plant cells and plants regenerated therefrom substantially resistant to infection by PLRV. In particular, the CaMV35S promoter, the enhanced CaMV35S promoter as described in Kay et al. (1987) and the FMV35S promoter are useful in the present invention. The FMV35S promoter (SEQ ID NO. 6) is particularly advantageous when used to drive expression of an operably coupled modified or synthetic modified PLRV coat protein structural DNA sequence. Use of the FMV35S promoter causes high expression of the modified PLRV coat protein DNA sequence in potato cells to provide potato plants that are highly resistant to infection by PLRV.

The FMV35S promoter (SEQ ID NO. 6) causes high expression of a gene coupled thereto in all types of cells within the stem section of the potato plant. In experiments using a β-Glucuronidase scoreable marker, expression was high in the cortical parenchyma, vascular cambium, primary and secondary xylem, primary phloem, internal phloem and pith parenchyma cells. Expression levels are higher than those observed with an enhanced CaMV35S promoter and are more uniform across different cell types. Similar results were observed in experiments with tubers, roots and leaves. Expression of the β-Glucuronidase gene driven by the FMV35S promoter (SEQ ID NO. 6) was observed in all cell types and at high levels, whereas expression driven by an enhanced CaMV35S was predominantly in the vascular bundles with lower levels of expression elsewhere.

The nucleotide sequence of a preferred FMV35S promoter is provided in FIG. 5 and is identified as SEQ ID NO 6. Those skilled in the art will know that other promoters can be used with advantageous results and are within the scope of this invention.

The glutamine synthetase (GS) promoter (Edwards et al. 1990) is useful for driving expression of PLRV coat protein genes because of the high levels of β-glucuronidase (GUS) expression observed in the vascular tissue of potato plants transformed with pMON8492, a plasmid containing the β-glucuronidase reporter gene driven by the glutamine synthetase promoter. GUS expression was analyzed by histochemical staining in stems, roots, leaves and tubers of 13 transgenic plants containing pMON8492. In stem sections of transgenic potato plants, strong GUS expression was observed in different cell types within the vascular tissue. Endodermis, primary phloem, xylem parenchyma, and internal phloem exhibited high levels of expression. All cell types within the phloem, such as sieve tube members, companion cells and phloem parenchyma cells showed expression. Expression was high in sieve tube members. Expression was not detected in vascular cambium or in xylem vessels. Leaves, roots, and tubers of these plants expressed high levels of GUS predominantly in the vascular bundles. In general, with glutamine synthetase promoter, strong expression is exhibited in the vascular tissues of the plants. Low variation was observed in the level of expression among the different transgenic plants examined.

A physical map of pMON8492 is presented in FIG. 13. This plasmid contains the following DNA segments. Starting from the bottom of FIG. 13 and moving counterclockwise, the 0.26 kb 3′ non-translated region of the nopaline synthase gene (NOS 3′) (Fraley et al. 1983), the β-glucuronidase gene (GUS:1) a reporter gene used for expression analysis, and the 1.26 kb glutamine synthetase promoter (GS) (Edwards et al. 1990) are provided. A 0.75 kb origin of replication from the RK2 plasmid (ori-V) (Stalker et al. 1981) and a chimeric kanamycin resistance gene engineered for plant expression to allow selection of transformed tissue is also provided. The chimeric gene consists of the 0.35 kb cauliflower mosaic virus 35S promoter (p-35s) (Odell et al. 1985), the 0.83 kb neomycin phosphotransferase type II gene (KAN), and the 0.26 kb 3′ non-translated region of the nopaline synthase gene (NOS 3′). Next is the 0.93 kb fragment isolated from transposon Tn7 which encodes bacterial spectinomycin/streptomycin resistance (Spc/Str) which is a determinant for selection in *E. coli* and *Agrobacterium tumefaciens* (Fling et al. 1985). The next coding segment consists of the modified potato leafroll virus coat protein gene (MOD-PLRV) (SEQ ID NO 4) driven by 1.22 kb of the GS promoter. The GS promoter was reduced by 0.04 kb to remove glutamine synthetase coding sequence and to provide an enzyme restriction site. The 0.64 kb of modified PLRV coat protein coding sequence is followed by the E9 3′ region from the pea small subunit RUBISCO gene (Coruzzi et al. 1984). Next is the 0.36 kb PvuI to BclI fragment from pTiT37 plasmid which contains the nopaline type T-DNA right border region (Fraley et al. 1985). It is joined to the 3.1 kb SalI to PvuI segment of pBR322 which provides the origin of replication for maintenance in *E. coli* (ori-322), and the bom site for the conjugational transfer into the *Agrobacterium tumefaciens* cells. Agro The mRNA produced by a DNA construct of the present invention also contains a 5′ non-translated leader sequence. This sequence can be derived from the promoter selected to express the gene and can be specifically modified to increase translation of the mRNA. The 5′ non-translated regions can also be obtained from viral RNAs, from suitable eukaryotic genes, or from a synthetic gene sequence. The present invention is not limited to constructs, as presented in the following examples, wherein the non-translated region is derived from both the 5' non-translated sequence that accompanies the promoter sequence and part of the 5' non-translated region of the virus coat protein gene. Rather, the non-translated leader sequence can be derived from an unrelated promoter or coding sequence as described.

The 3' non-translated region of the chimeric plant gene contains a polyadenylation signal which functions in plants to cause the addition of polyadenylated nucleotides to the 3' end of the RNA. Examples of suitable 3' regions are the 3' transcribed, non-translated regions containing the polyadenylation signal of Agrobacterium tumor inducing (Ti) plasmid genes, such as the nopaline synthase (NOS) gene, and plant genes such as the soybean storage protein genes and the small subunit of the ribulose-1,5-bisphosphate carboxylase (ssRUBISCO) gene. An example of a preferred 3' region is that from the ssRUBISCO gene from pea (referred to as E9 3') as described in the Examples to follow.

The modified or synthetic modified PLRV coat protein DNA sequences of the present invention can be inserted into any plant. Infection by PLRV is particularly problematic in plants of the family Solanaceae which includes potato, tobacco, tomato and peppers. PLRV is a particular problem in potato plants and this invention has particular utility in potato. This invention can be used with any potato variety, such as Russet Burbank, Russet Norkotah, Desiree, Bintje, Alpha, Superior, Norchip, Atlantic and Shepody. Preferred potato varieties for use in connection with the present invention are Russet Burbank, Russet Norkotah, Norchip, Atlantic and Shepody.

A plant transformation vector containing one of the PLRV coat protein DNA sequences of this invention can be introduced into the desired plant by any suitable method. *Agrobacterium tumefaciens* mediated transformation is known to be effective with members of the Solanaceae family of plants and is particularly useful. Other transformation methods such as electroporation, microprojectile or particle gun technology, liposomes, and chemicals that increase free DNA uptake may also be used.

*Agrobacterium* mediated transformation has proved to be particularly useful for the transformation of potato. A vector containing a PLRV coat protein DNA sequence is first introduced into a disarmed Agrobacterium strain. This is accomplished by mobilizing the desired vector into an ABI Agrobacterium strain by the triparental conjugation system using the helper plasmid pRK2013 (Ditta et al., 1980). The binary ABI strain is the chloramphenicol resistant derivative of *Agrobacterium tumefaciens* A208 which carries the disarmed Ti plasmid pTiC58 (Koncz and Schell 1986). The Ti plasmid does not carry the T-DNA phytohormone genes and the strain is therefore unable to cause crown gall disease. The disarmed Ti plasmid provides the trfA gene functions required for autonomous replication of the vector after conjugation into the ABI strain. When the plant tissue is incubated with the ABI::transformation vector conjugate, the vector is transferred to the plant cells by the vir functions encoded by the disarmed pTiC58 plasmid. The pTiC58 Ti plasmid does not transfer to the plant cells, but remains in the Agrobacterium. Both single and double border transformation vectors may be delivered to the plant via the ABI strain. The single border vector opens at the T-DNA right border region and the entire vector sequence is inserted into the host plant chromosome. The right border is lost during transfer and integration. In a double border vector, the T-DNA segment between the right and left border region is transformed to the plant cell, therefore delivering only the chimeric genes of interest to the chromosome. The remainder of the vector and the border sequences are lost during transfer and integration.

Transformation of potato cells using an *Agrobacterium* mediated transformation protocol has been accomplished. Two protocols are described below, but those skilled in the art know that modifications and optimization to the protocols can be made. Agrobacterium containing the desired plant transformation vector is grown overnight in 2 mls of LBSCK broth. LBSCK contains 10 g NaCl, 5 g yeast extract, 10 g Bacto-Typtone, 50 mg spectinomycin, 25 mg Chloramphenicol and 50 mg Kanamycin in a 1 liter volume, pH 7.0. The following day, the bacteria is diluted 1:10 with MSO or until an OD (optical density) reading of 0.2–0.3 is established. MSO contains 4.4 g MS salts (Sigma), 30 g sucrose and 2 ml $B_5$ vitamin (500X) in a 1 liter volume, pH 5.7. Leaves from the stem of potato plants that have been grown under sterile conditions for about three (3) weeks on PM media supplemented with 25 mg/l ascorbic acid are removed. PM media contains 4.4 g MS salts (Sigma), 30 g sucrose, 0.17 g $NaH_2PO_4 \cdot H_2O$, 1 ml thiamine HCl and 0.1 g Inositol in a 1 liter volume, pH 6.0 and 0.2% Gelrite agar. The stems are placed on a vegetable slicer (~30–50 at a time) and cut into 3–5mm segments. These stem explants are inoculated for 15 minutes with the diluted bacteria. Approximately 20 mls of bacterial solution is used per 1000 stem explants. The bacterial solution is removed by aspiration and the explants placed onto prepared co-culture plates. The co-culture plates contain 1/10 MSO with 1.5 mls of TxD cells overlayed with wetted filter paper. Approximately 50 explants are placed on each plate.

After a two (2) day co-culture period, explants are placed onto callus induction plates containing MSO plus 0.5 mg/1ZR (Seatin riboside), 10mg/1 $AgNO_3$ and 0.1mg./1 NAA (naphthaleneacetic acid) for four (4) weeks. These plates also contain 100mg/1 kanamycin to select for transformed cells. After four (4) weeks, explants that exhibit growth in the presence of kanamycin are placed on shoot induction media which contains MSO plus 5.0mg/1 ZR, 10mg/1 $AgNO_3$ and 0.3mg/1 $GA_3$ (gibberellic acid) and 100mg/1 kanamycin for further selection. Shoots typically begin to appear at about six (6) weeks. The plants are then placed in sundae cups with PM media and allowed to grow for approximately 2 weeks. Plants are placed into soil, hardened off, and analyzed to verify transformation by assaying for the presence of a protein which confers resistance to the antibiotic kanamycin to the plant. If the plant is positive for expression of the protein, the plant is kept for further study and maintained in tissue culture.

Alternately, the explants may be placed on callus induction plates containing MSO plus 3.0 mg./1 BA (6 Benzylaminopurine) and 0.01 mg/1 NAA for four (4) week 100 mg./1 kanamycin for selection. For shoot induction, the explants are placed on MSO plus 0.3 mg/1 $GA_3$ only and 100 mg/ml kanamycin for selection. Shoots begin to appear at about 8 weeks. Shoots are recallused on MSP-5 with 200 mg/ml kanamycin and assayed in two weeks. MSP-5 contains 4.4 g MS salts (Sigma), 5 ml SLLX vitamins (200×), 30 g sucrose, 2.25 ml BAP, 0.186 ml NAA in 1 liter, pH 5.6 and 0.2% Gelrite agar.

After the plant has been transformed and after transformed callus has been identified, the transformed callus tissue is regenerated into whole plants. Any known method of regeneration for members of Solanaceae, and particularly methods for regenerating potato plants, can be used in this invention.

It has further been found, as will be described in more detail in the Examples to follow, that potato plants that have been transformed to express two genes containing the modified PLRV coat protein (SEQ ID NO. 4) DNA sequence provide a high frequency of resistant plants. The two genes containing the modified PLRV coat protein (SEQ ID NO. 4) DNA sequence are preferably placed in a single transformation vector under the control of different or the same promoters. A preferred double gene construct comprises a first gene construct comprising the FMV35S promoter (SEQ ID NO. 6) driving expression of a modified PLRV coat protein (SEQ ID NO. 4) structural DNA sequence and an appropriate 3. non-translated polyadenylation signal coupled with a second gene construct comprising an enhanced CaMV35S promoter (ECaMV35S or E35S) driving the expression of a modified PLRV coat protein (SEQ ID NO. 4) structural DNA sequence and an appropriate 3' non-translated polyadenylation signal. It is believed that the differential tissue specificities of the FMV35S and the E35S promoters or the glutamine synthetase promoter provides for a more efficient or complete expression of the modified PLRV coat protein (SEQ ID NO. 4) in the necessary tissues of the plant which provides the high frequency of resistant plants when a double gene construct is used. A plant transformation vector containing a double modified PLRV coat protein (SEQ ID NO. 4) gene construct as described above can be prepared using routine procedures and methods that are known and available to those skilled in the art of plant genetic engineering.

Nucleotide sequence analysis of other members of the luteovirus group such as Barley yellow dwarf virus (Miller et al. 1988), beet western yellow virus (Veidt et al. 1988) and a preliminary report on soybean dwarf virus and carrot red leaf virus (Martin et al. 1990) indicates that the organization of their genomes is similar to PLRV. In these viruses as well, the coat protein open reading frame encompasses another internal open reading frame which would translate a protein of about 17kd molecular weight. The coat protein open reading frame is also followed by another open reading frame which is separated from the coat protein by an amber termination codon. It would, therefore, be possible to make the alterations to the internal translation initiation codons and terminator codon as described for PLRV in the coat protein sequences of other luteoviruses such as those above to obtain resistance to these viruses in their host plants.

The following examples are provided to better elucidate the practice of the present invention and should not be interpreted in any way to limit the scope of the present invention. Those skilled in the art will recognize that various modifications can be made to the methods and genes described herein while not departing from the spirit and scope of the present invention.

EXAMPLE 1

Figure 7:
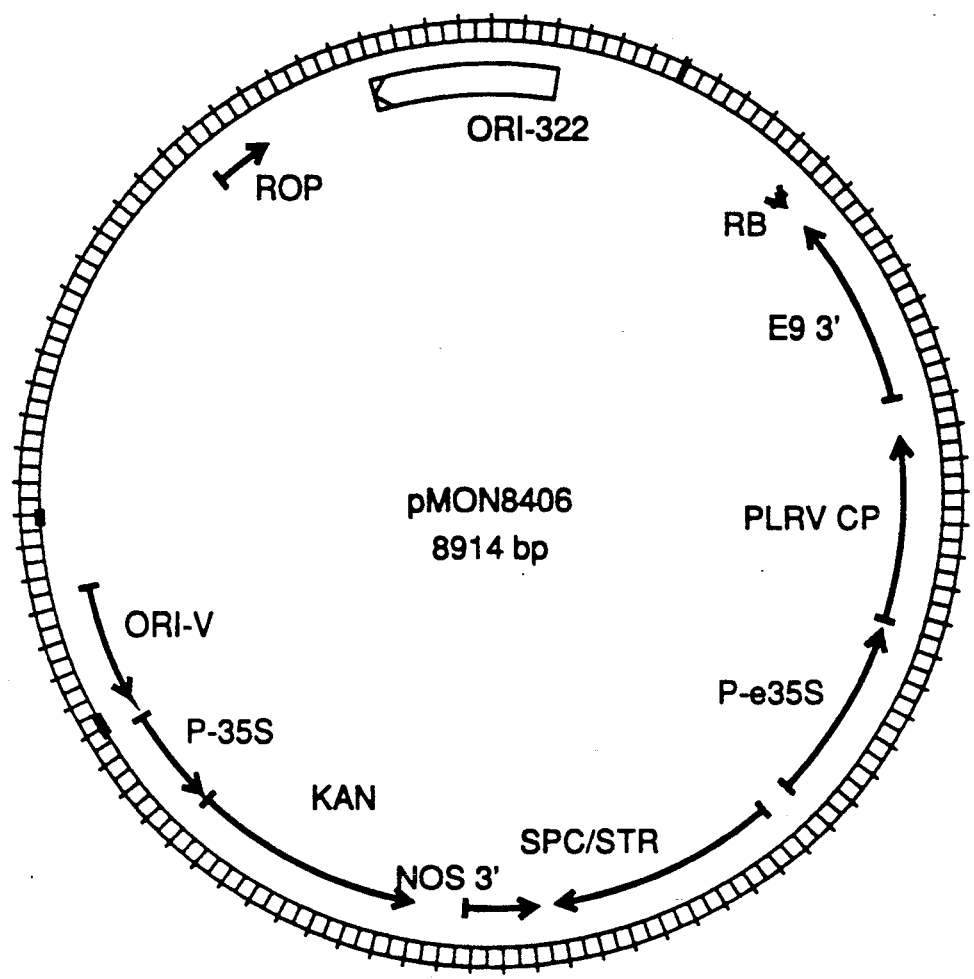
FIG. 7 illustrates a physical map of the plasmid pMON8406.

The DNA coding sequence for a native PLRV coat protein (SEQ ID NO. 1) was engineered into plant transformation vector pMON906 to study its ability to confer resistance to PLRV in plants expressing the native PLRV coat protein (SEQ ID NO. 1). A physical map of pMON906 is presented in FIG. 6. The resulting vector is identified as pMON8406 and is illustrated in FIG. 7.

This plant transformation vector contains the neomycin phosphotransferase II gene driven by the CaMV35S promoter and terminated by the nopaline synthase 3' region and the native PLRV coat protein gene driven by the enhanced CaMV35S promoter and terminated by the pea small subunit gene E9 3' region. The vector was mated into Agrobacterium ACO by a triparental plasmid transfer method involving pRK2013 (Ditta et al. 1980). The resulting Agrobacterium was used in a plant transformation protocol to introduce pMON8406 into Russet Burbank potato using the procedure described above which uses a callus induction media containing 3.0 mg/1 BA and 0.01 mg/1 NAA in MSO, a shoot induction media containing 0.3 mg/1 GA$_3$ in MSO and a shoot recallusing step on MSP-5. Potato plants regenerated from this protocol were selected on kanamycin then rooted and potted in soil. Two weeks after potting, leaf disks were homogenized with a Teflon ® tissue grinder each in 250 μl of 2×SDS extraction buffer. Aliquots were loaded onto a PAGE apparatus and the presence of coat protein was analyzed by western analysis. Protein bands corresponding in size to PLRV coat protein and reacting with a polyclonal antibody made to PLRV virions were observed on the western blot. The presence of PLRV antigen in the transgenic, regenerated potato plantlets was also detected which is conclusive of expression of the PLRV coat protein gene.

All transgenic lines derived from transformation with pMON8406 were assayed by northern analysis to determine the presence of PLRV coat protein mRNA corresponding to the predicted mRNA transcript expected from pMON8406. Transgenic potato lines containing pMON8452, pMON8449 and pMON8468 (as described in the Examples to follow) were also assayed for the presence of RNA or protein by northern analysis and western analysis, respectively. Table I shows that a larger percentage of lines containing the modified (SEQ ID NO. 1) or modified synthetic (SEQ ID NO. 5) PLRV coat protein gene have detectable levels of RNA or protein as compared to plants expressing the native PLRV coat protein (SEQ ID NO. 1) sequence.

TABLE I

| Construct | assayed for | | |
|---|---|---|---|
| | #KAN+ lines | RNA/protein | #expressors |
| pMON8406 | 99 | 99 | 10 |
| pMON8452/ pMON8449 | 86 | 57 | 29 |
| pMON8468 | 23 | 14 | 8 |

Those plants with detectable coat protein RNA or protein were propagated to provide plants for a test of the transgenic plant's resistance to infection by PLRV. Green peach aphids were used to inoculate potato plants with PLRV. A PLRV infected Physalis leaf with viruliferous aphids was placed on each of the test plants and aphids were allowed to remain for 5 days before spraying with insecticide. Twenty-five (25) plants from each plant line were challenged with PLRV. The plants were then transplanted to the field.

Leaves from pMON8406 transgenic potato plants were assayed by punching discs from upper leaves with a cork borer at 28 days post inoculation (dpi), 42 dpi, 56 dpi and 77 dpi. These leaf discs were analyzed for the presence of PLRV antigen and the incidence of infection by ELISA. The results of this test are shown in Table II. Russet Burbank Idaho (RBID) is the wild type control and 623 is the transgenic potato plants expressing the native PLRV coat protein. The data shows that after 77 dpi, PLRV was aphid transmitted to 92% of the control plants. The transgenic line 623 was 68% infected. The level of virus antigen was also significantly reduced in those transgenic plants that became infected throughout the test.

TABLE II

| LINE | % INFECTED PLANTS Days post inoc. | | | | AVERAGE VIRUS ANTIGEN (ng/mg[1]) Days post inoc. | | | |
|---|---|---|---|---|---|---|---|---|
| | 28 | 42 | 56 | 77 | 28 | 42 | 56 | 77 |
| RBID | 64 | 72 | 80 | 92 | 3.98 | 3.21 | 1.04 | 4.23 |
| 623 | 40 | 52 | 52 | 68 | 2.10 | 1.01 | 0.62 | 2.55 |

[1]ng PLRV/mg leaf tissue

Analysis of other transgenic potato lines containing native PLRV coat protein (SEQ ID NO. 1) indicated 100% infection when challenged with PLRV.

EXAMPLE 2

Figure 8:
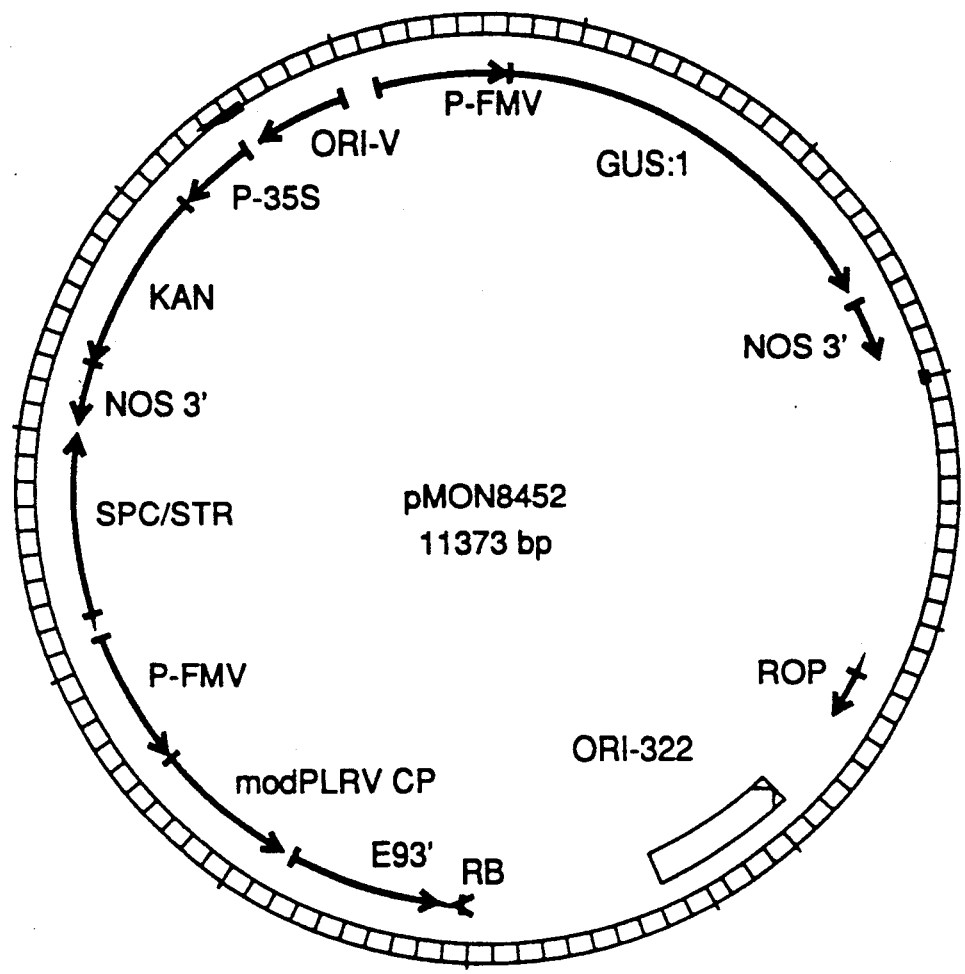
FIG. 8 illustrates a physical map of the plasmid pMON8452.

The modified PLRV coat protein (SEQ ID NO. 4) structural DNA sequence was inserted into a plant transformation vector identified as pMON8452 to study the ability of the modified PLRV coat protein (SEQ ID NO. 4) DNA sequence to confer resistance to PLRV in plants expressing the modified DNA sequence. A physical map of this plasmid is illustrated in FIG. 8.

Plasmid pMON8452 contains the following DNA segments. Starting from the bottom of FIG. 8 and going counter-clockwise, the 0.26 kb (kilobase) 3, non-translated region of the nopaline synthase gene (NOS 3') (Fraley et al. 1983), the β-glucuronidase gene (GUS:1) a reporter gene used to identify transformed plants, and the 0.64 kb E35S promoter from the cauliflower mosaic virus (CaMV) (Kay et al. 1987) are provided. A 0.75 kb origin of replication from the RK2 plasmid (ori-V) (Stalker et al. 1981) and a chimeric kanamycin resistance gene engineered for plant expression to allow selection of transformed tissue is also provided. The chimeric gene consists of the 0.35 kb cauliflower mosaic virus 35S promoter (P-35S) (Odell et al. 1985), the 0.83 kb neomycin phosphotransferase type II gene (KAN), and the 0.26 kb 3' non-translated region of the nopaline synthase gene (NOS 3') (Fraley et al. 1983). Next is the 0.93 kb fragment isolated from transposon Tn7 which encodes bacterial spectinomycin/streptomycin resistance (Spc./Str) which is a determinant for selection in E. coli and Agrobacterium tumefaciens (Fling et al. 1985). The next coding segment consists of the modified potato leafroll virus coat protein gene (PLRV cp) (SEQ ID, NO 4) driven by 0.62 kb of the FMV35S promoter (SEQ ID NO. 6). The 0.64 kb of modified PLRV coat protein (SEQ ID NO. 4) coding sequence is followed by the E9 3' region from the pea small subunit RUBISCO gene (Coruzzi et al. 1984). Next is the 0.36 kb PvuI to BclI fragment from pTiT37 plasmid, which contains the nopaline type T-DNA right border region (Fraley et al. 1985). It is joined to the 3.1 kb SalI to PvuI segment of pBR322 which provides the origin of replication for maintenance in E. coli (ori-322), and the bom site for the conjugational transfer into the Agrobacterium tumefaciens cells.

Figure 9:
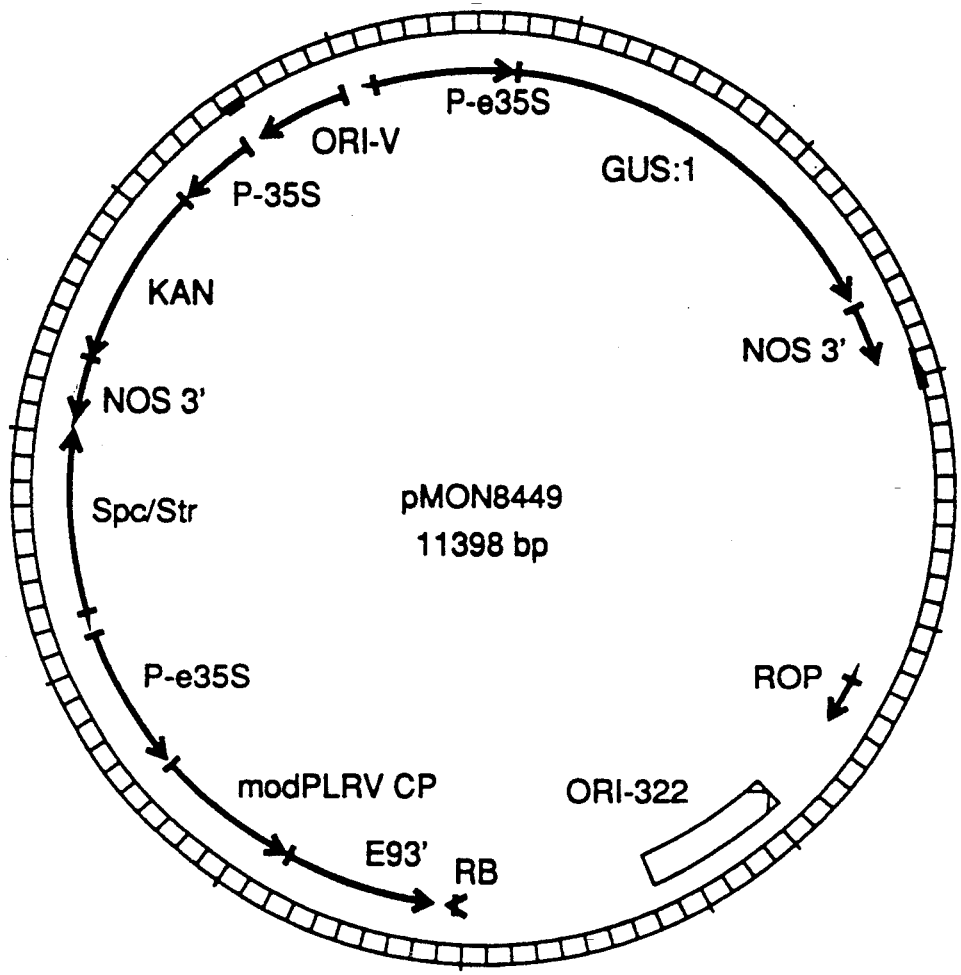
FIG. 9 illustrates a physical map of the plasmid pMON8449.

The modified PLRV coat protein (SEQ ID NO. 4) structural DNA sequence was also inserted into a second plant transformation vector identified as pMON8449 for the same purposes. A physical map of this plasmid is illustrated in FIG. 9.

Plasmid pMON8449 contains the following DNA segments. Starting from the bottom of FIG. 9 and going counter-clockwise, the 0.26 kb (kilobase) 3' non-translated region of the nopaline synthase gene (NOS 3') (Fraley et al. 1983), the β-glucuronidase gene (GUS:1) a reporter gene used to identify transformed plants, and the 0.64 kb E35S promoter from the cauliflower mosaic virus (ECaMV35S) (Kay et al. 1987) are provided. A 0.75 kb origin of replication from the RK2 plasmid (ori-V) (Stalker et al. 1981) and a chimeric kanamycin resistance gene engineered for plant expression to allow selection of transformed tissue. The chimeric gene consists of the 0.35 kb cauliflower mosaic virus 35S promoter (P-35S) (Odell et al. 1985), the 0.83 kb neomycin phosphotransferase type II gene (KAN), and the 0.26 kb 3' non-translated region of the nopaline synthase gene (NOS 3') (Fraley et al. 1983). Next is the 0.93 kb fragment isolated from transposon Tn7 which encodes bacterial spectinomycin/streptomycin resistance (Spc/Str) which is a determinant for selection in E. coli and Agrobacterium tumefaciens (Fling et al. 1985). The next coding segment consists of a modified potato leafroll virus coat protein gene (PLRV cp) (SEQ ID NO 4) driven by the E35S promoter. The 0.64 kb of modified PLRV coat protein (SEQ ID NO 4) coding sequence is followed by the E9 3' region from the pea small subunit RUBISCO gene (Coruzzi et al. 1984). Next is the 0.36 kb PvuI to BclI fragment from pTiT37 plasmid, which contains the nopaline type T-DNA right border region (Fraley et al. 1985). It is joined to the 3.1 kb SalI to PvuI segment of pBR322 which provides the origin of replication for maintenance in E. coli (ori-322), and the bom site for the conjugational transfer into the Agrobacterium tumefaciens cells.

These plasmids, pMON8452 and pMON8449, were mobilized into the ABI Agrobacterium strain as previously described and transformed into Russet Burbank by the procedure described in Example 1. Transformed plants were confirmed by selection on kanamycin recalusing media. The regenerated plants were assayed for expression of RNA and protein from pMON8449 and pMON8452 vectors. RNA of the expected size was detected in the transgenic potato plants and coat protein expression was detected by western analysis.

The kanamycin resistant potato plants were propagated and challenged with PLRV viruliferous green peach aphids as described in Example 1. Twenty-three (23) plant lines containing pMON8449 and thirty-five (35) plant lines containing pMON8452 were tested. A plant line consists of between 10–40 plants, usually about 20 plants. The % infected value of a plant line is determined by the number of plants in a plant line that had detectable PLRV antigen determined by ELISA, at any level, assayed 5 weeks post inoculation. For example, if a plant line contained 10 plants and one of those plants became infected after challenge with PLRV while the remaining 9 plants showed no infection, that plant line would have a 10% Infected value and would be counted in the 0–20% Infected category. A plant line in the 0–20% Infected category is considered highly resistant and a plant line in the 21–60% Infected category is considered very resistant. Seven transgenic plant lines expressing the FMV35S (SEQ ID NO 6)

driven modified PLRV coat protein (SEQ ID NO 4) DNA sequence were highly resistant to infection by PLRV. One transgenic line expressing the E35S driven modified PLRV coat protein (SEQ ID NO 4) sequence was highly resistant to PLRV infection. These results are tabulated below in Table III.

TABLE III

| CONSTRUCT | #LINES | % INFECTED | | |
|---|---|---|---|---|
| | | 0-20 | 21-60 | 61-100 |
| pMON8449 | 23 | 1 | 3 | 19 |
| pMON8452 | 35 | 7 | 5 | 23 |

EXAMPLE 3

Figure 10:
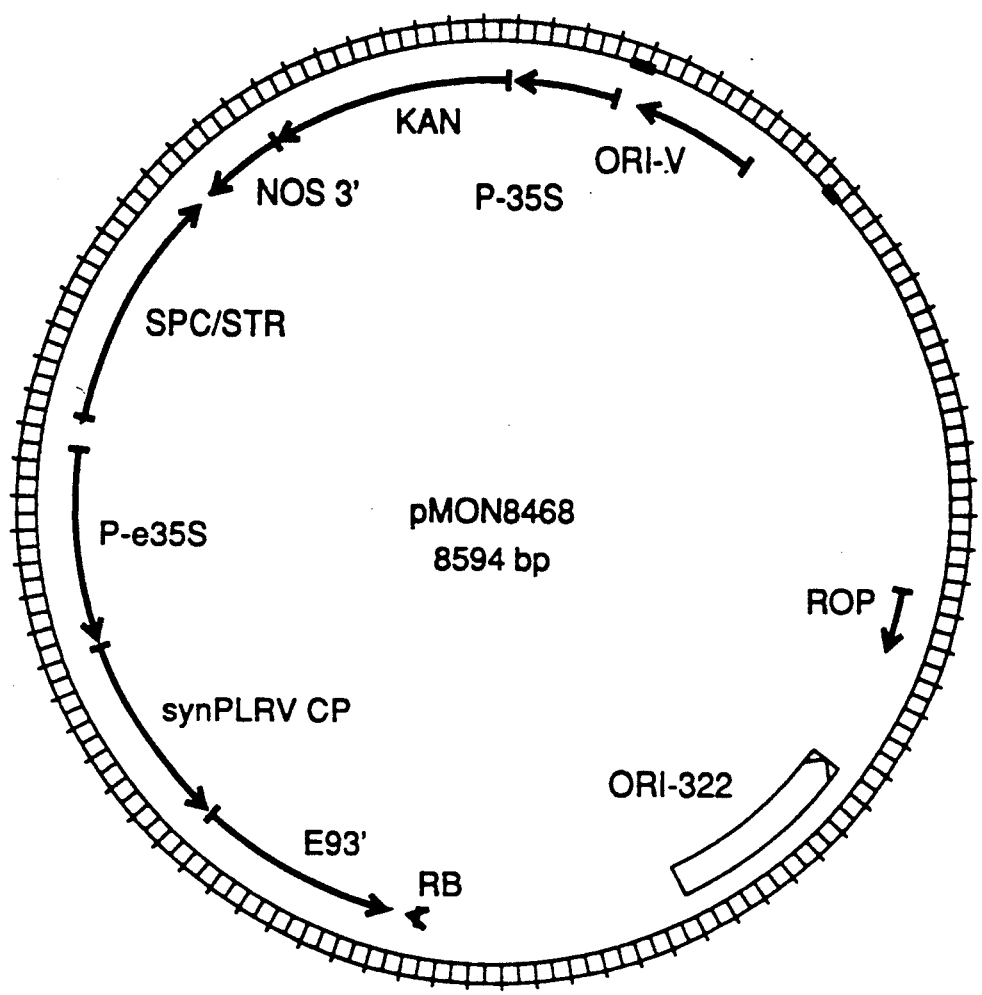
FIG. 10 illustrates a physical map of the plasmid pMON8468.

The synthetic modified PLRV coat protein (SEQ ID NO 5) structural DNA sequence was inserted into a plant transformation vector to obtain pMON8468 which was transformed into potato plants to study the ability of this DNA sequence to confer resistance to PLRV. A physical map of this plasmid is illustrated in FIG. 10.

Plasmid pMON8468 contains the following DNA segments. Starting from the bottom of FIG. 10 and going counter-clockwise, the 0.75 kb origin of replication from the RK2 plasmid (ori-V) (Stalker et al. 1981) is provided. A chimeric kanamycin resistance gene engineered for plant expression to allow selection of the transformed tissue is also provided. The chimeric gene consists of the 0.35 kb cauliflower mosaic virus 35S promoter (P-35S) (Odell et al. 1985), the 0.83 kb neomycin phosphotransferase type II gene (KAN), and the 0.26 kb 3' non-translated region of the nopaline synthase gene (NOS 3') (Fraley et al. 1983). Next is the 0.93 kb fragment isolated from transposon Tn7 which encodes bacterial spectinomycin/streptomycin resistance (Spc/Str), which is a determinant for selection in E. coli and *Agrobacterium tumefaciens* (Fling et al. 1985). The next coding segment consists of the synthetic modified potato leafroll virus coat protein gene (synPLRV cp) (SEQ ID NO 5) driven by the E35S promoter. The 0.64 kb of synthetic modified PLRV coat protein coding sequence is followed by the E9 3' region from the pea small subunit RUBISCO gene (Coruzzi et al. 1984). Next is the 0.36 kb PvuI to BclI fragment from pTiT37 plasmid, which contains the nopaline type T-DNA right border region (Fraley et al. 1985). It is joined to the 3.1 kb SalI to PvuI segment of pBR322 which provides the origin of replication for maintenance in *E. coli* (ori-322), and the bom site for the conjugational transfer into the Agrobacterium tumefaciens cells.

Plasmid pMON8468 was transformed into potato stem segments by the procedure described in Example 1.

Transgenic Russet Burbank plants resulting from the Agrobacterium mediated transformation method were assayed by northern and western analysis for the presence of mRNA and protein from the synthetic modified PLRV coat protein (SEQ ID NO 5) gene. The northern analysis showed expression of RNA from the pMON8468 vector by specific hybridization of a PLRV coat protein probe to a RNA band on the blot. Western analysis showed the specific reaction of a protein band corresponding to the molecular weight of PLRV coat protein isolated from virions.

Eighteen (18) transgenic Russet Burbank potato lines containing pMON8468 were challenged with PLRV by inoculation with viruliferous aphids as described in Example 1. The results show no lines in the highest resistance level category, 0-20% Infected. The synthetic modified PLRV coat protein (SEQ ID NO 5) DNA sequence does not appear to be a significant improvement over the modified PLRV coat protein (SEQ ID NO 4) DNA sequence when expression is driven by the E35S promoter. These results are presented in Table IV.

TABLE IV

| #LINES | % INFECTED | | |
|---|---|---|---|
| | 0-20 | 21-60 | 61-100 |
| 18 | 0 | 1 | 17 |

EXAMPLE 4

A plant vector containing a double modified PLRV coat protein (SEQ ID NO 40 gene construct was prepared and transformed into potato plant cells to determine the effectiveness of a double gene construct to confer resistance to infection by PLRV in transgenic plants expressing the double gene construct. A physical map of pMON8517, a plasmid containing a double gene construct, is illustrated in FIG. 1.

Figure 11:
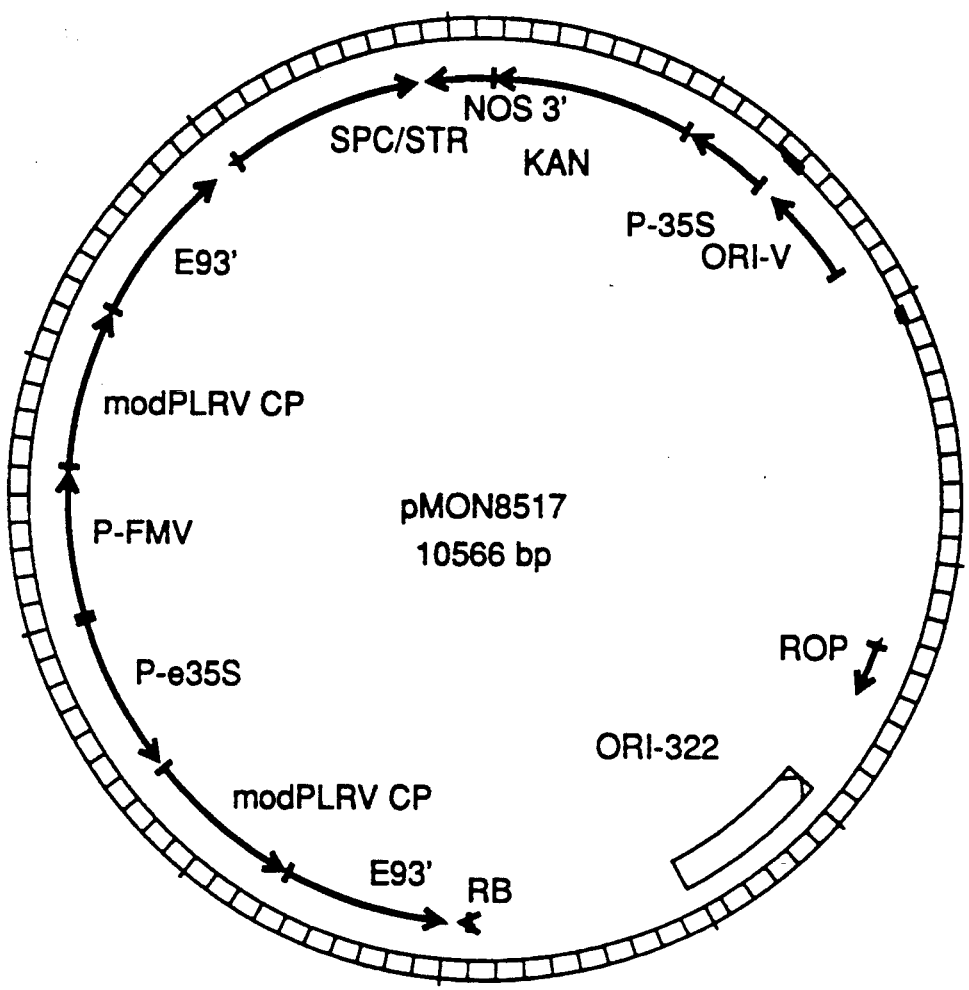
FIG. 11 illustrates a physical map of the plasmid pMON8517.

The pMON8517 plasmid contains the following DNA segments. From the bottom moving counter-clockwise in FIG. 11, the 0.75 Kb origin of replication from the RK2 plasmid (ori-V) (Stalker et al. 1981) is provided. The chimeric kanamycin resistance gene engineered for plant expression to allow selection of the transformed tissue is also provided and consists of the 0.35 Kb cauliflower mosaic virus 35S promoter (P-35S) (Odell et al. 1985), the 0.83 Kb neomycin phosphotransferase type II gene (KAN), and the 0.26 Kb 3' non-translated region of the nopaline synthase gene (NOS 3') (Fraley et al. 1983). A 0.93 Kb fragment isolated from transposon Tn7 which encodes bacterial spectinomycin/streptomycin resistance (Spc/Str), and is a determinant for selection in *E. coli* and *Agrobacterium tumefaciens* (Fling et al. 1985) is also present. The next genetic elements are in a clockwise orientation in the plasmid and consists of the modified potato leafroll virus coat protein gene (PLRV cp) (SEQ ID NO 4) driven by the FMV promoter (SEQ ID NO 6). This 0.64 kb of PLRV cp coding sequence is modified to remove the translational start for a 17kd open reading frame internal to the PLRV cp start and a more efficient translational terminator added (SEQ ID NO 4). The promoter is the 35S promoter of figwort mosaic virus (FMV) (SEQ ID NO 6) (Gowda et al. 1989), followed by the PLRV coat protein gene and the E9 3' terminator region from pea rubisco (Coruzzi, et al., 1984). The next coding segment consists of the modified potato leafroll virus coat protein gene (SEQ ID NO 4) described above, driven by the e35S promoter of cauliflower mosaic virus (Kay et al. 1987) and terminated by the E9 3' region of pea rubisco. The orientation of the promoters and PLRV coat protein genes are such that the promoters are adjacent to each other and direct transcription in opposite directions. Next is the 0.36 Kb PvuI to BclI fragment from the pTiT37 plasmid, which contains the nopaline-type T-DNA right border region (Fraley et al. 1985). It is joined to the 3.1 Kb SalI to PvuI segment of pBR322 which provides the origin of replication for maintenance in *E. coli* (ori-322), and the bom site for the conjugational transfer into the *Agrobacterium tumefaciens* cells.

The pMON8517 vector was mobilized into the ABI Agrobacterium strain. The ABI strain is the A208 Agrobacterium tumefaciens carrying the disarmed Ti plasmid pTiC58 (Koncz and Schell 1986). The Ti plasmid does not carry the T-DNA phytohormone genes, and the strain is therefore unable to cause the crown gall disease. Mating of pMON8517 into ABI was done by the triparental conjugation system using the helper plasmid pRK2013 (Ditta et al. 1980). When the plant tissue is incubated with the ABI::pMON8517 conjugate, the vector is transferred to the plant cells by the vir functions encoded by the disarmed pTiC58 plasmid.

Figure 12:
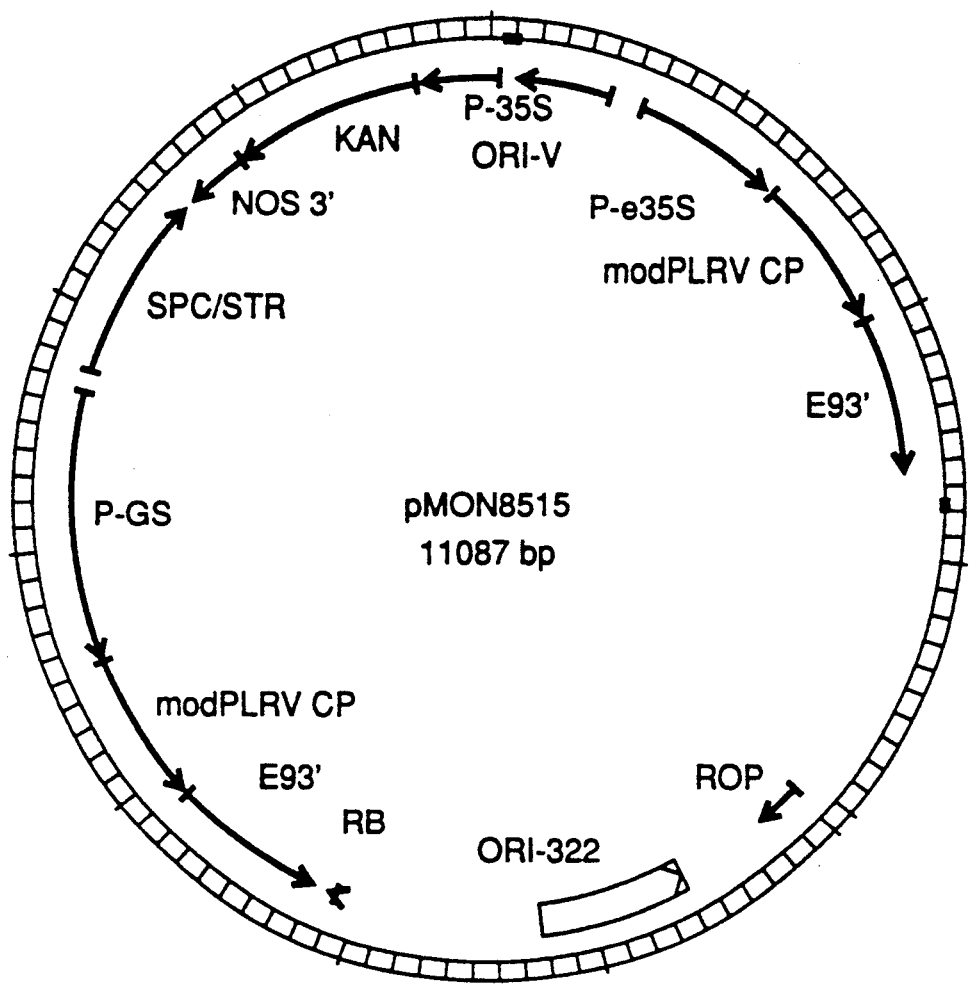
FIG. 12 illustrates a physical map of the plasmid pMON8515.
Figure 13:
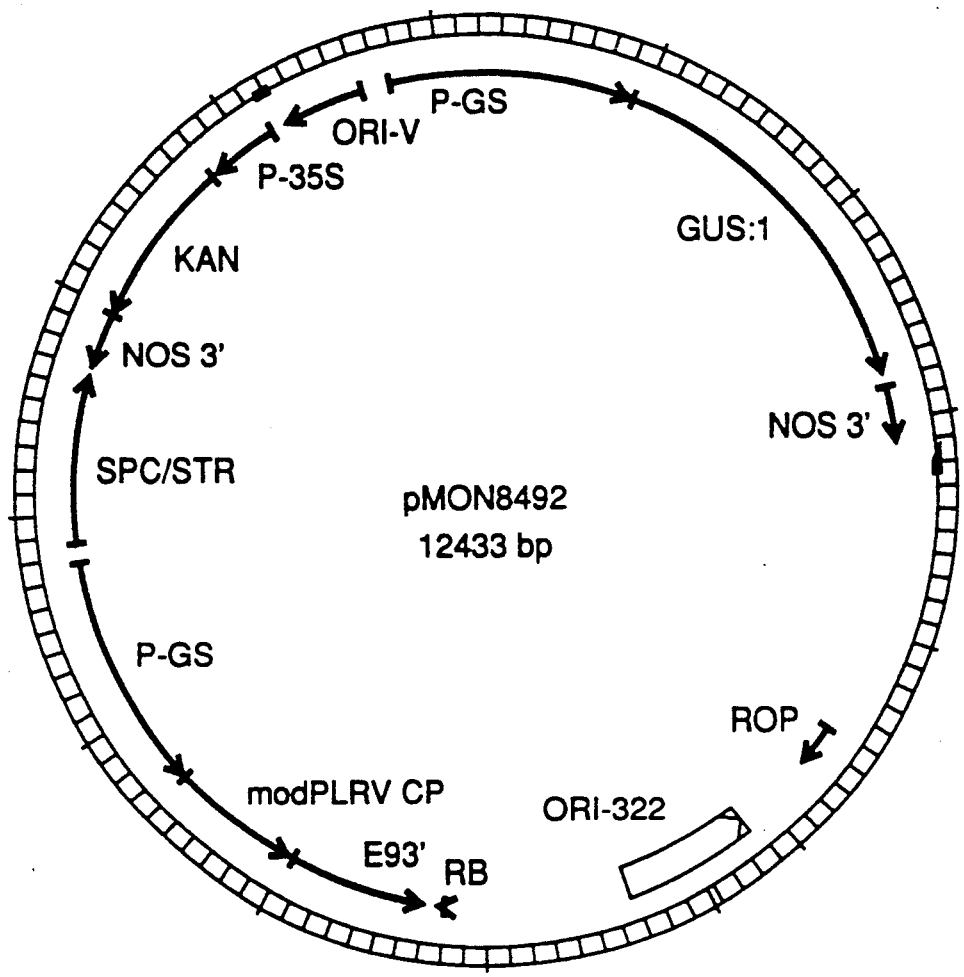
FIG. 13 illustrates a physical map of the plasmid pMON8492.

The pMON8515 plasmid contains the following DNA segments. From the bottom moving counter-clockwise in FIG. 12, the E9 3' terminator region from pea rubisco (Coruzzi et al. 1984), the 0.64 kb of potato leafroll virus coat protein gene (PLRV CP) modified to remove the translational start for a 17 kd open reading frame internal to the PLRV coat protein start and a more efficient translational terminator added (SEQ ID NO 4). The promoter is 0.65 kb of the e35s CaMV promoter (Gowda et al. 1989). The 0.75 Kb origin of replication from the RK2 plasmid (ori-V) (Stalker et al. 1981) is provided. The chimeric kanamycin resistance gene engineered for plant expression to allow selection of the transformed tissue is also provided and consists of the 0.35 Kb cauliflower mosaic virus 35S promoter (P-35S) (Odell et al. 1985), the 0.83 Kb neomycin phosphotransferase type II gene (KAN), and the 0.26 Kb 3' non-translated region of the nopaline synthase gene (NOS 3') (Fraley et al. 1983). A 0.93 Kb fragment isolated from transposon Tn7 which encodes bacterial spectinomycin/streptomycin resistance (Spc/Str), and is a determinant for selection in E. coli and Agrobacterium tumefaciens (Fling et al. 1985) is also present. The next coding segment consists of the modified potato leafroll virus coat protein gene (PLRV cp) (SEQ ID NO 4) driven by the glutamine synthetase (GS) promoter. This 0.64 kb of PLRV cp coding sequence is modified to remove the translational start for a 17kd open reading frame internal to the PLRV cp start and a more efficient translational terminator added (SEQ ID NO 4). The promoter is 1.2 kb of the GS3A promoter region of the glutamine synthetase gene from pea (Edwards et al. 1990), followed by the PLRV coat protein gene and the E9 3' terminator region from pea rubisco (Coruzzi, et al., 1984). Next is the 0.36 Kb PvuI to BclI fragment from the pTiT37 plasmid, which contains the nopaline-type T-DNA right border region (Fraley et al. 1985). It is joined to the 3.1 Kb SalI to PvuI segment of pBR322 which provides the origin of replication for maintenance in E. coli (ori-322), and the bom site for the conjugational transfer into the Agrobacterium tumefaciens cells.

The pMON8515 vector was mobilized into the ABI Agrobacterium strain. The ABI strain is the A208 Agrobacterium tumefaciens carrying the disarmed Ti plasmid pTiC58 (Koncz and Schell 1986). The Ti plasmid does not carry the T-DNA phytohormone genes, and the strain is therefore unable to cause the crown gall disease. Mating of pMON8515 into ABI was done by the triparental conjugation system using the helper plasmid pRK2013 (Ditta et al. 1980). When the plant tissue is incubated with the ABI::pMON8515 conjugate, the vector is transferred to the plant cells by the vir functions encoded by the disarmed pTiC58 plasmid. The vector opens at the T-DNA right border region, and the entire pMON8515 vector sequence is inserted into the host plant chromosome. The pTiC58 Ti plasmid does not transfer to the plant cells, but remains in the Agrobacterium.

These vectors were transformed into potato stem segments by the protocol described above utilizing a callus induction media containing 5.0mg/ml ZR, 10mg/ml AgNO$_3$ and 0.1 mg/ml NAA in MSO for 4 weeks. The shoot induction media used included 5.0mg/ml ZR, 10mg/ml AgNO$_3$ 0.3mg/1 GA$_3$ in MSO. Kanamycin was used throughout for selection. Transgenic plants resulting from the Agrobacterium mediated transformation method were assayed by northern and western analysis for the presence of mRNA and protein from the double gene construct containing the modified PLRV coat protein (SEQ ID NO 4) DNA sequence. Northern analysis showed expression of RNA from pMON8517 by specific hybridization of a PLRV coat protein probe to a RNA band on the blot. Western analysis showed the specific reaction of a protein band corresponding to the molecular weight of PLRV coat protein isolated from virions.

Sixty (60) transgenic Russet Burbank potato lines containing pMON8517 and forty-two (42) transgenic Russet Burbank potato lines containing pMON8515 were challenged with PLRV viruliferous aphids in a field test conducted at Parma, Idaho. These lines were contained in four (4) separate plantings and inoculations. Transgenic lines and Russet Burbank wild-type plants were inoculated with PLRV when a leaf containing PLRV viruliferous aphids was placed on each plant. Forty (40) plants per line were tested in two replicated sets of twenty (20) plants each six weeks after inoculation. A plant is determined to be highly resistant if 4 or less plants of the 40 have detectable PLRV antigen by ELISA. The ratio of the number of plants with detectable PLRV antigen over the number of plants inoculated with viruliferous PLRV aphids is expressed as the infection rate. Across the four plantings, the % infection of Russet Burbank wild-type plants ranged from 56% to 75%. The results in Table V show a statistically significant reduction in infection rate of transgenic potato plants expressing a double modified PLRV coat protein (SEQ ID NO 40) gene construct six (6) weeks after challenge.

TABLE V

| | # lines tested | # highly resistant |
|---|---|---|
| pMON8517 | 60 | 9 |
| | line # | Infection Rate |
| pMON8517 | 2040 | 0/40 |
| | 2054 | 0/40 |
| | 2057 | 1/40 |
| | 2080 | 1/40 |
| | 2060 | 2/40 |
| | 2055 | 2/40 |
| | 2058 | 2/40 |
| | 2059 | 3/40 |
| | 2046 | 3/40 |
| Control | RBId | 40/80 |
| | # lines tested | # highly resistant |
| pMON8515 | 42 | 4 |
| | line # | Infection Rate |
| | 2039 | 1/40 |
| | 2038 | 1/40 |
| | 2053 | 3/40 |
| | 2034 | 4/40 |

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

REFERENCES

1. Abel et al. 1986, Science 232:738–743.
2. Aoyagi et al. 1988, Mol. Gen. Genet. 213:179–185.
3. Bahner et al. 1990, J. Gen. Virol. 71(10):2251–2256.
4. Bevan M. 1984, Nucleic Acids Res. 12(22):8711–8721.
5. Coruzzi et al. 1984, EMBO J. 3:1671.
6. Cuozzo et al. 1988, Bio/Technology 6:549–557.
7. Ditta et al. 1980, Proc. Natl. Acad. Sci. USA 77:7347–7351.
8. Edwards et al. 1990, Proc. Natl. Acad. Sci. 87:3459–3463.
9. Fling et al. 1985, Nucleic Acids Res. 13(19):7095–7106.
10. Fraley et al. 1983, Proc. Natl. Acad. Sci. USA 80:4803–4807.
11. Fraley et al. 1985, Bio/Technology 3:629–635.
12. Gowda et al. 1989, Journal of Cellular Biochemistry Supplement 13D, 301 (Abstract).
13. Hemenway et al. 1988, EMBO J. 7:1273–1280.
14. Herrera-Estrella et al. 1983, Nature 303:209.
15. Hunkapiller et al. 1983, Methods in Enzymol. 91:399–413.
16. Kawchuk et al. 1989, J. Gen. Virol. 70:783–788.
17. Kawchuk et al. 1990, Mol. Plant-Microbe Interactions 3(5):301–307.
18. Kay et al. 1987, Science 236:1299–1302.
19. Klee H.J. et al. 1985, Bio./Technology 3:637–42.
20. Koncz and Schell 1986, Mol. Gen. Genet. 204:383–396.
21. Kunkel et al. 1987, Methods in Enzymol. 154:307–382.
22. Lawson et al. 1990, Bio./Technology 8:127–134.
23. Martin et al. 1990, Annu. Rev. Phytopathol. 28:341–363.
24. Miller et al. 1988, Virology 165:306–309.
25. Odell et al. 1985, Nature 313:810–812.
26. Powell et al. 1990, Virology 175:124–30.
27. Prill et al. 1988, J. Gen. Virol. 69:2397–2402.
28. Smith et at. 1988, Phytopathology 78:1060–1066.
29. Stalker et al. 1981, Mol. Gen. Genet. 181:8–12.
30. Stark and Beachy 1989, Bio/Technology 7:1257–1262.
31. Sugaya et al. 1989, Plant Cell Physiol. 3:649–654.
32. Van der Wilk et al. 1989, FEBS LET 245:51–56.
33. Van Dun et al. 1988, Virology 164:383–89.
34. Veidt et al. 1988, Nuc. Acids. Res. 16:9917–9932.
35. Yang et al. 1990, Proc. Natl. Acad. Sci. 87:4144–4148.

What is claimed is:

1. A modified DNA sequence encoding a potato leafroll virus coat protein which comprises a native potato leafroll virus coat protein DNA sequence having at least one internal translation initiation codon in a different reading frame than said native potato leafroll virus coat protein DNA sequence altered to a noninitiator codon.

2. The DNA sequence of claim 1 further comprising a TAA termination condon which is positioned at the 3' end of said potato leafroll virus coat protein DNA sequence.

3. The DNA sequence of claim 2 further comprising a TAG codon following said TAA termination codon.

4. The DNA sequence of claim 1 wherein at least one of said internal translation initiation codons begins at nucleotide 26 of said native potato leafroll virus coat protein DNA sequence.

5. The DNA sequence of claim 1 wherein at least one of said internal translation initiation codons begins at nucleotide 32 of said native potato leafroll virus coat protein DNA sequence.

6. The DNA sequence of claim 1 wherein at least one of said internal translation initiation codons is the start of a 17kd open reading frame internal to said native potato leafroll virus coat protein DNA sequence and in a different reading frame.

7. The DNA sequence of claim 1 wherein a plurality of internal translation initiation codons in a different reading frame than said native potato leafroll virus coat protein DNA sequence are altered to non-initiator codons.

8. The DNA sequence of claim 7 wherein said internal translation initiation codons begin at nucleotide 26 and nucleotide 32 of said native potato leafroll virus coat protein DNA sequence.

9. A DNA sequence encoding a potato leafroll virus coat protein having the sequence of SEQ ID NO 4.

10. A DNA sequence encoding a potato leafroll virus coat protein having the sequence of SEQ ID NO 5.

11. A plant gene comprising:
a full-length transcript promoter from figwort mosaic virus;
a structural DNA sequence encoding a potato leafroll virus coat protein which comprises a native potato leafroll virus coat protein DNA sequence having at least one internal translation initiation codon in a different reading frame than said native potato leafroll virus coat protein DNA sequence altered to a non-initiator codon; and
a 3' non-translated DNA sequence which functions in plants to cause the addition of polyadenylated nucleotides to the 3' end of the transcribed sequence.

12. The plant gene of claim 11 wherein said full-length transcript promoter from figwort mosaic virus has the sequence corresponding to SEQ ID NO 6.

13. The plant gene of claim 11 further comprising a 5' non-translated leader sequence.

14. The plant gene of claim 11 wherein said structural DNA sequence encoding a potato leafroll virus coat protein further comprises a TAA termination condon which is positioned at the 3' end of said potato leafroll virus coat protein DNA sequence.

15. The plant gene of claim 14 wherein said structural DNA sequence encoding a potato leafroll virus coat protein further comprises a TAG codon following said TAA termination codon.

16. The plant gene of claim 11 wherein at least one of said internal translation initiation codons of said structural DNA sequence begins at nucleotide 26 of said native potato leafroll virus coat protein DNA sequence.

17. The plant gene of claim 11 wherein at least one of said internal translation initiation codons of said structural DNA sequence begins at nucleotide 32 of said native potato leafroll virus coat protein DNA sequence.

18. The plant gene of claim 11 wherein at least one of said internal translation initiation codons is the start of a 17kd open reading frame internal to said native potato leafroll virus coat protein DNA sequence and in a different reading frame.

19. The plant gene of claim 11 wherein a plurality of internal translation initiation codons in a different reading frame than said native potato leafroll virus coat protein DNA sequence are altered to non-initiator codons.

20. The plant gene of claim 19 wherein said internal translation initiation codons of said structural DNA sequence begin at nucleotide 26 and nucleotide 32 of said native potato leafroll virus coat protein DNA sequence.

21. The plant gene of claim 11 wherein said structural DNA sequence encoding a potato leafroll virus coat protein is selected from the group consisting of SEQ ID NO 4 and SEQ ID NO 5.

22. A method for modifying a native potato leafroll virus coat protein DNA sequence to enhance the expression of potato leafroll virus coat protein in plants comprising:
altering translation initiation sites in said native potato leafroll virus coat protein DNA sequence which are internal to and in a different reading frame than said native potato leafroll virus coat protein DNA sequence to non-initiator codons.

23. The method of claim 22 further comprising the step of providing a TAA termination codon at the end of said native potato leafroll virus coat protein DNA sequence.

24. The method of claim 22 wherein said translation initiation sites are internal ATG codons at the start of a 17kd open reading frame internal to said native potato leafroll virus coat protein DNA sequence and in a different reading frame.

25. The method of claim 22 wherein said translation initiation sites begin at nucleotides 26 and 32 of said native potato leafroll virus coat protein DNA sequence.

26. The method of claim 22 wherein said native potato leafroll virus coat protein DNA sequence is further altered to utilize plant preferred DNA sequences and condons.

27. A method for providing resistance to a potato plant from infection by potato leafroll virus comprising the steps of:
transforming said potato plant with a DNA sequence encoding a potato leafroll virus coat protein which comprises a native potato leafroll virus coat protein DNA sequence having at least one internal translation initiation codon in a different reading frame than said native potato leafroll virus coat protein DNA sequence modified to a non-initiator codon; and
selecting transformed potato plants which express said potato leafroll virus coat protein at a level sufficient to render said plants resistant to infection by 28. The method of claim 27 wherein said modified potato leafroll virus coat protein DNA sequence further comprises a TAA termination condon which is positioned at the 3' end of said potato leafroll virus coat protein DNA sequence.

29. The method of claim 27 wherein said internal translation initiation codons begin at nucleotide 26 and nucleotide 32 of said native potato leafroll virus coat protein DNA sequence.

30. The method of claim 27 wherein said potato plant is selected from the group of potato varieties consisting of Russet Burbank, Russet Norkotah, Desiree, Bintji, Alpha, Superior, Norchip, Atlantic and Shepody.

31. The method of claim 27 wherein said potato plant variety is Russet Burbank.

32. A DNA sequence comprising:

a first plant gene comprising a promoter capable of causing expression in plant cells;

a structural DNA sequence encoding a potato leafroll virus coat protein which comprises a native potato leafroll virus coat protein DNA sequence have at least one internal translation initiation condon in a different reading frame than said native potato leafroll virus coat protein DNA sequence altered to a non-initiator condon; and a 3' non-translated DNA sequence which functions in plants to cause the addition of polyadenylated nucleotides to the 3' end of the transcribed sequence; and a second plant gene comprising promoter capable of causing expression in plant cells;

a structural DNA sequence encoding a potato leafroll virus coat protein which comprises a native potato leafroll virus coat protein DNA sequence having at least one internal translation initiation condon in a different reading frame than said native potato leafroll virus coat protein DNA sequence altered to a non-initiator condon; and a 3' non-translated DNA sequence which functions in plants to cause the addition of polyadenylated nucleotides to the 3' end of the transcribed sequence.

33. THE DNA sequence of claim 32 wherein said structural DNA sequence of said first and second plant genes further comprises a TAA termination condon which is positioned at the 3' end of said potato leafroll virus coat protein DNA sequence.

34. The DNA sequence of claim 33 further comprising a TAG condon following said TAA termination condon.

35. The DNA sequence of claim 32 wherein at least one of said internal translation initiation condons of said structural DNA sequence of said first and second plant genes begins at nucleotide 26 of said native potato leafroll virus coat protein DNA sequence.

36. The DNA sequence of claim 32 wherein at least one of said internal translation initiation condons of said structural DNA sequence of said first and second plant genes begins at nucleotide 32 of said native potato leafroll virus coat protein DNA sequence.

37. The DNA sequence of claim 32 wherein at least one of said internal translation initiation condons of said structural DNA sequence of said first and second internal to said native potato leafroll virus coat protein DNA sequence and in a different reading frame.

38. The DNA sequence of claim 32 wherein a plurality of internal translation initiation condons of said structural DNA sequence of said first and second plant genes in a different reading frame than said native potato leafroll virus coat protein DNA sequence are altered to non-initiator condons.

39. The DNA sequence of claim 38 wherein said internal translation initiation condons begin at nucleotide 26 and nucleotide 32 of said native potato leafroll virus coat protein DNA sequence.

40. The DNA sequence of claim 32 wherein said structural DNA sequence of said first and second plant genes encoding a potato leafroll virus coat protein is selected from the group consisting of SEQ ID NO 4 and SEQ ID NO 5.

41. A DNA sequence comprising:
a first plant gene comprising an enhanced 35S promoter from cauliflower mosaic virus;

a structural DNA sequence encoding a potato leafroll virus coat protein having the sequence of SEQ ID NO 4; and an E9 3' non-translated region from the pea small subunit RUBISCO gene; and a second plant gene comprising a 35S promoter from the figwort mosaic virus;

a structural DNA sequence encoding a potato leafroll virus coat protein having the sequence of SEQ ID NO 4; and an E9 3' non-translated region from the pea small subunit RUBISCO gene.

42. A DNA sequence comprising:
a first plant gene comprising a 35S promoter from cauliflower mosaic virus;

a structural DNA sequence encoding a potato leafroll virus coat protein having the sequence of SEQ ID NO 4; and an E9 3' non-translated region from the pea small subunit RUBISCO gene; and a second plant gene comprising a glutamine synthetase GS3A promoter from pea;

a structural DNA sequence encoding a potato leafroll virus coat protein having the sequence of SEQ ID NO 4; and an E9 3' non-translated region from the pea small subunit RUBISCO gene.

43. A potato plant comprising the DNA sequence of claim 1.

44. A potato plant comprising SEQ ID NO 4.

45. A potato plant comprising SEQ ID NO 5.

46. A potato tuber comprising the DNA sequence of claim 1.

47. A potato tuber comprising SEQ ID NO 4.

48. A potato tuber comprising SEQ ID NO 5.

* * * * *